(12) United States Patent  
Nomura

(10) Patent No.: US 9,607,909 B2  
(45) Date of Patent: Mar. 28, 2017

(54) ANALYSIS DEVICE, ANALYSIS METHOD, FILM FORMATION DEVICE, AND FILM FORMATION METHOD

(71) Applicant: FUJITSU LIMITED, Kawasaki-shi, Kanagawa (JP)

(72) Inventor: Kenji Nomura, Atsugi (JP)

(73) Assignee: FUJITSU LIMITED, Kawasaki (JP)

(*) Notice: Subject to any disclaimer, the term of this patent is extended or adjusted under 35 U.S.C. 154(b) by 345 days.

(21) Appl. No.: 14/293,008

(22) Filed: Jun. 2, 2014

(65) Prior Publication Data

US 2015/0011024 A1   Jan. 8, 2015

(30) Foreign Application Priority Data

Jul. 8, 2013   (JP) .................................. 2013-142658

(51) Int. Cl.
*H01L 21/66* (2006.01)
*G01N 23/22* (2006.01)

(52) U.S. Cl.
CPC .............. *H01L 22/26* (2013.01); *H01L 22/14* (2013.01); *G01N 23/22* (2013.01); *G01N 2223/315* (2013.01); *G01N 2223/602* (2013.01)

(58) Field of Classification Search
CPC .... G01N 23/22; G01N 23/083; G01N 23/087; G01N 2223/325; G01N 2223/602; G01N 23/02; G01N 23/06; G01N 23/223; H01L 22/14; H01L 22/16; G06T 2207/10116; G06T 2207/30148

(Continued)

(56) References Cited

U.S. PATENT DOCUMENTS 3,418,467 A * 12/1968 Ladell .................... G21K 1/06  
378/119  
4,104,519 A * 8/1978 Oldendorf ............ G01N 23/223  
378/113

(Continued)

FOREIGN PATENT DOCUMENTS

JP   6-27056    2/1994  
JP   7-283284   10/1995

(Continued)

OTHER PUBLICATIONS

JPOA—Office Action mailed on Feb. 7, 2017 issued with respect to the basic Japanese Patent Application No. 2013-142658, with full machine translation.

*Primary Examiner* — Mary Wilczewski  
(74) *Attorney, Agent, or Firm* — Fujitsu Patent Center

(57) ABSTRACT

An analysis device includes an X-ray generation part configured to generate four monochromatic X-rays with different energies to irradiate a sample, an electrically conductive sample stage configured to place the sample thereon and formed of an electrically conductive material, an electrode configured to detect an electric current carried by irradiating the sample with the four monochromatic X-rays with different energies, and an electric power source configured to apply a voltage between the electrically conductive sample stage and the electrode, wherein the four monochromatic X-rays with different energies are X-rays included within a range from an absorption edge of a compound semiconductor included in the sample to a higher energy side of 300 eV.

8 Claims, 16 Drawing Sheets

(58) Field of Classification Search
USPC ......... 438/5, 12; 118/712; 378/58, 156, 157, 378/158
See application file for complete search history.

(56) References Cited

U.S. PATENT DOCUMENTS

| | | | | |
|---|---|---|---|---|
| 4,567,605 | A * | 1/1986 | Bartels | G01N 23/2076 378/82 |
| 4,821,301 | A * | 4/1989 | Cocks | G01N 23/20 378/70 |
| 5,491,738 | A * | 2/1996 | Blake | G01N 23/207 378/49 |
| 5,657,363 | A * | 8/1997 | Hossain | G01N 23/223 378/44 |
| 5,742,658 | A * | 4/1998 | Tiffin | G01N 23/20 257/E21.53 |
| 5,754,620 | A * | 5/1998 | Hossain | G01N 23/223 378/44 |
| 5,778,039 | A * | 7/1998 | Hossain | G01N 23/20008 378/44 |
| 5,932,896 | A * | 8/1999 | Sugiura | B82Y 20/00 257/102 |
| 6,376,267 | B1 * | 4/2002 | Noack | B82Y 15/00 378/70 |
| 6,512,811 | B2 * | 1/2003 | Fujioka | G01N 23/06 378/51 |
| 2002/0131550 | A1 | 9/2002 | Fujioka et al. | |
| 2006/0055935 | A1 * | 3/2006 | Cheben | G01J 3/02 356/451 |
| 2006/0227087 | A1 * | 10/2006 | Hajjar | G09G 3/02 345/84 |
| 2007/0291896 | A1 * | 12/2007 | Parham | G01N 23/046 378/37 |
| 2010/0111262 | A1 * | 5/2010 | Lee | G21K 1/062 378/158 |
| 2010/0135463 | A1 * | 6/2010 | Kang | G01T 1/2018 378/98.9 |
| 2012/0039438 | A1 * | 2/2012 | Parham | A61B 6/032 378/62 |
| 2015/0011024 | A1 * | 1/2015 | Nomura | H01L 22/14 438/5 |
| 2015/0185170 | A1 * | 7/2015 | Adhiprakasha | G01N 23/223 216/55 |
| 2015/0361587 | A1 * | 12/2015 | Mikawa | C30B 7/105 423/409 |
| 2016/0077025 | A1 * | 3/2016 | Zhang | G01N 23/201 378/89 |

FOREIGN PATENT DOCUMENTS

| | | |
|---|---|---|
| JP | 2001-165851 | 6/2001 |
| JP | 2001-201469 | 7/2001 |
| JP | 2002-280433 | 9/2002 |
| JP | 2006-258771 | 9/2006 |
| JP | 2008-175766 | 7/2008 |
| JP | 2009-147271 | 7/2009 |
| JP | 2011-027528 | 2/2011 |
| JP | 2012-089651 | 5/2012 |

* cited by examiner

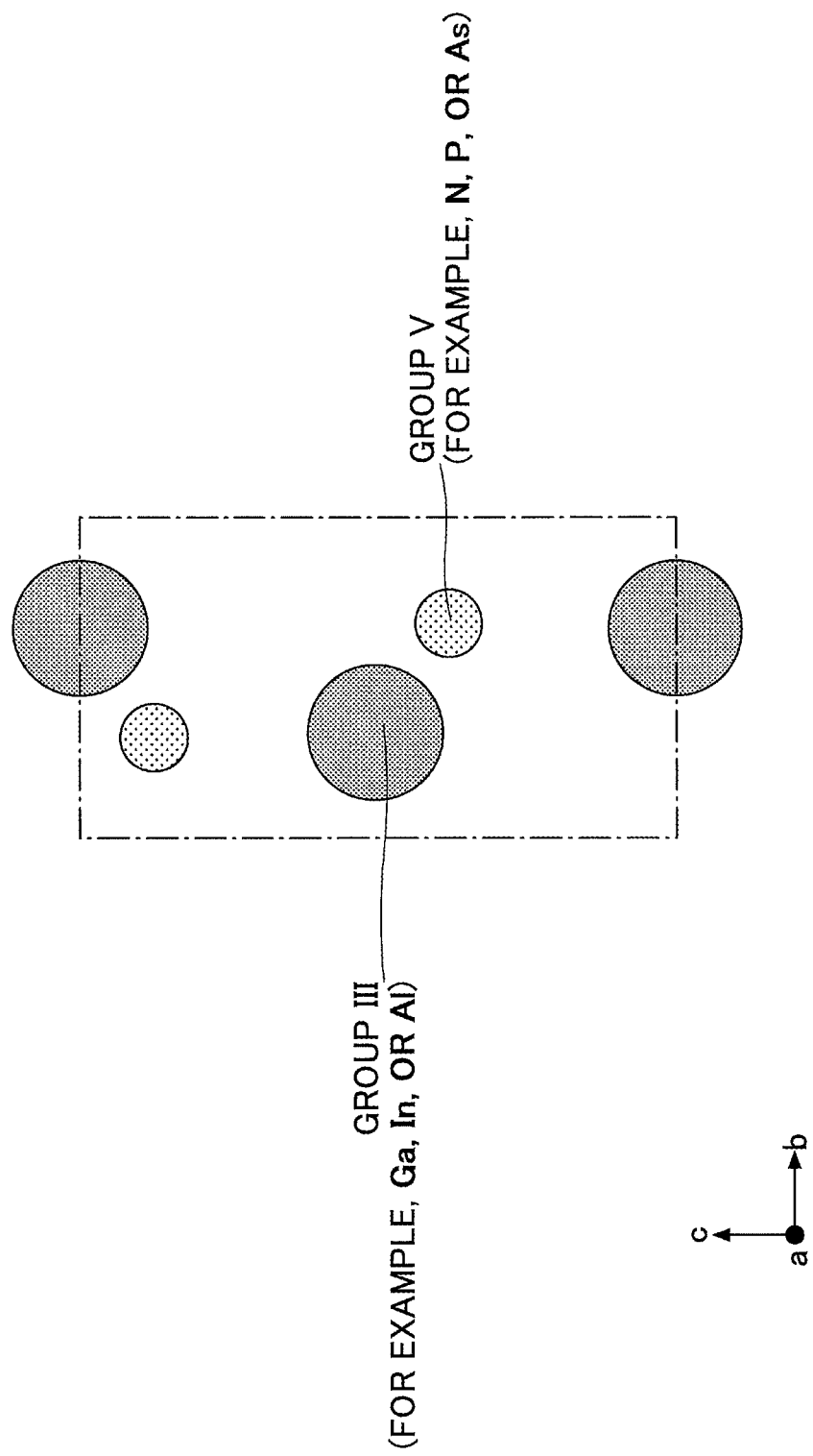

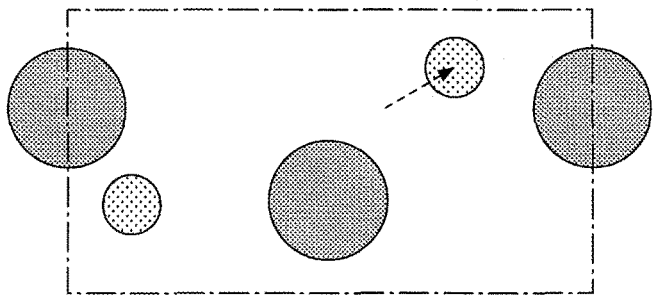
FIG.2A  Ga VACANCY
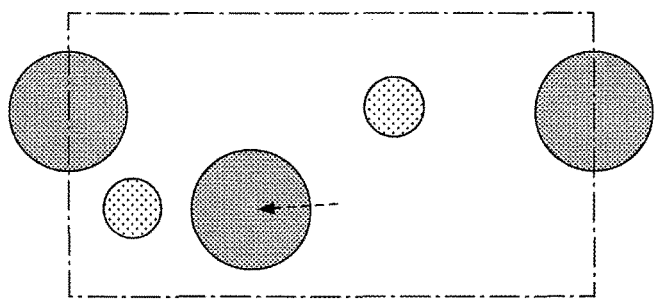
FIG.2B  N VACANCY
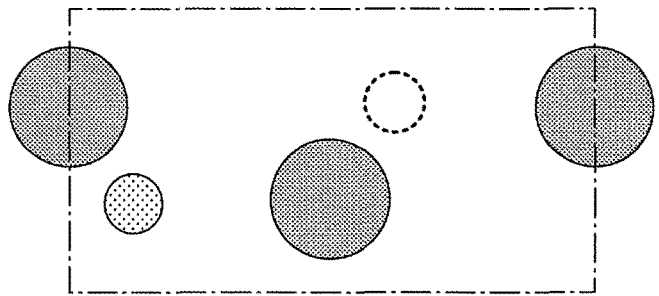
FIG.2C  Ga DISTURBANCE
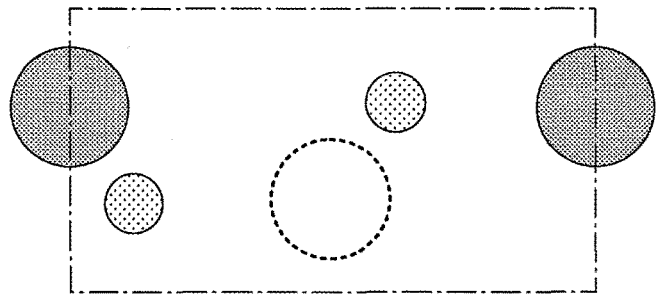
FIG.2D  N DISTURBANCE

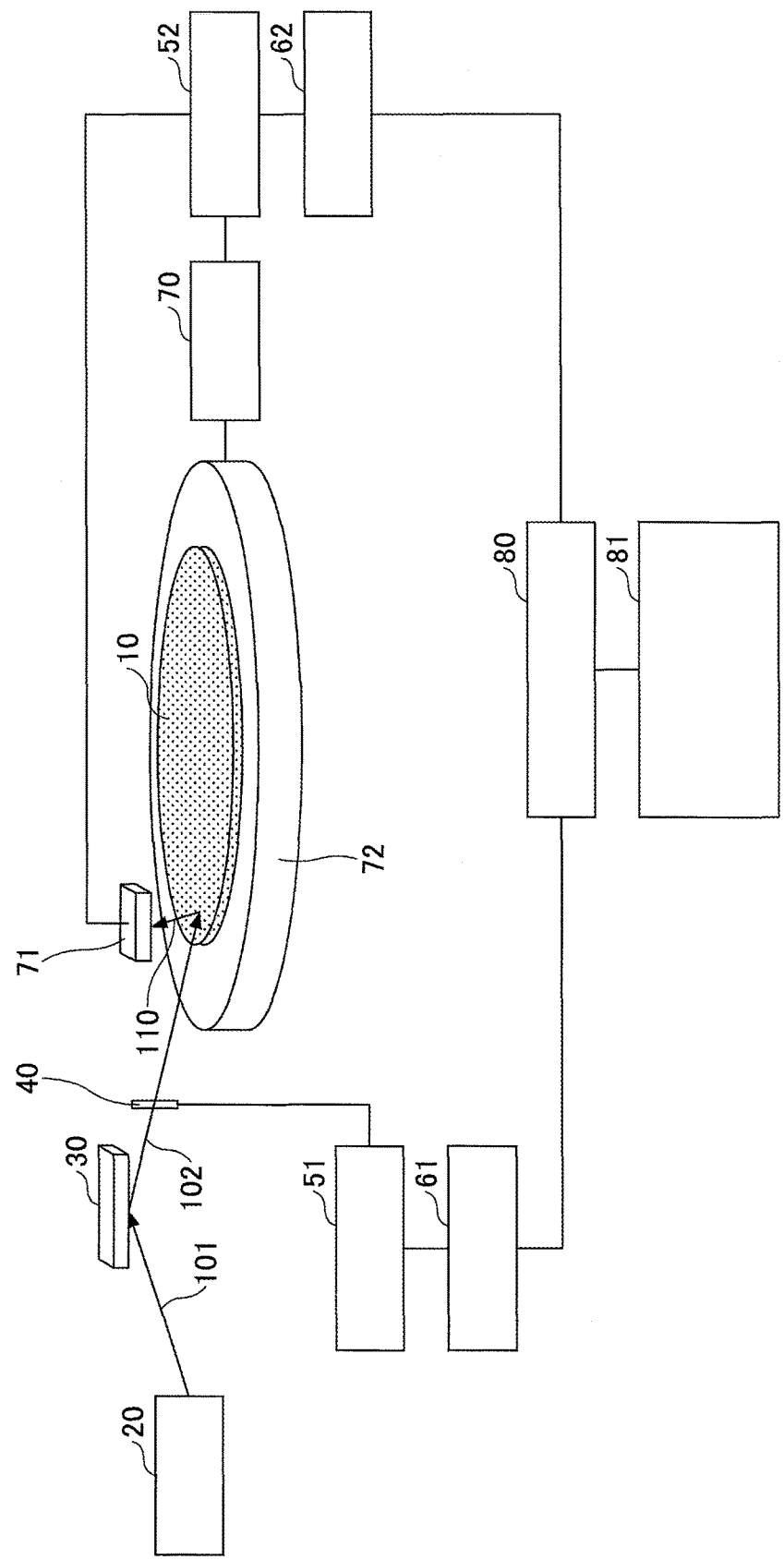

ANALYSIS DEVICE, ANALYSIS METHOD, FILM FORMATION DEVICE, AND FILM FORMATION METHOD

CROSS-REFERENCE TO RELATED APPLICATIONS

This application claims the benefit of priority to Japanese Patent Application No. 2013-142658 filed on Jul. 8, 2013, the entire contents of which are herein incorporated by reference.

FIELD

A certain aspect of the embodiments discussed herein relates to an analysis device, an analysis method, a film formation device, and a film formation method.

BACKGROUND

It is possible to use a III-V compound semiconductor for a semiconductor device such as a power device other than a light emitting diode (LED) or the like. For such a power device that uses a III-V compound semiconductor, there is provided a high electron mobility transistor (HEMT) that is composed of an electron supply layer and an electron transient layer. In an HEMT, a two-dimensional electron gas (2 DEG) is generated in an electron transient layer near an interface between an electron supply layer and the electron transient layer. Because an operation of such an HEMT is made by transfer of a 2 DEG in an electron transient layer, a high quality crystal film that is formed by an epitaxial growth is desired for the electron transient layer. Herein, a high quality crystal film means a state of no atomic vacancy and no disturbance of an atomic position. For an electron transient layer, a GaN film is frequently used that is a representative III-V compound semiconductor. In a case where a GaN film is used for an electron transient layer, an epitaxial growth is conducted by using a GaN substrate so that it is possible to readily obtain a high quality crystal film.

However, it is difficult to supply an HEMT that uses a GaN or the like at a low cost, because a GaN substrate is very expensive. For this reason, a method for forming a high quality GaN film via a buffer layer on a silicon carbide (SiC) substrate, a sapphire ($Al_2O_3$) substrate or even further an inexpensive silicon (Si) substrate has been attempted in recent years. An SiC substrate, an Si substrate, or the like is such that a lattice constant is different between a material for forming a substrate and a material for forming a film, differing from a GaN substrate. For this reason, in a case where lattice mismatch is large, disturbance of an atomic position in a film is large and further a vacancy may be frequently generated.

For a method for evaluating a disturbance of an atomic position in a GaN film or the like, an X-ray diffraction (XRD) method is commonly used. For example, a disturbance of a crystalline orientation in a direction vertical to a substrate surface is determined from a half-value width of a symmetric diffraction peak in a rocking curve measurement (tilt), and further, a disturbance of a crystalline orientation in an in-plane direction is determined from a half-value width of an asymmetric diffraction peak in an in-plane rotation measurement (twist). These values are correlated with a dislocation density, and frequently used as a method for evaluating a disturbance of an atomic position. However, an XRD is a very macroscopic measurement method, and hence, may be difficult to be sufficient in a case where an evaluation of a disturbance at a more atomic level is desired. Furthermore, in an XRD method, it is also impossible to distinguish and evaluate a disturbance of a group III element such as gallium (Ga) and a disturbance of a group V element such as nitrogen (N).

For a method for evaluating a vacancy in a GaN film or the like, a photo-luminescence (PL) method is commonly used. Specifically, an intensity of a yellow luminescence observed near a wavelength of 570 nm is sensitive to an amount of a vacancy of a group III element (Ga) and is commonly used. Moreover, an intensity of a luminescence at a band edge that does not depend on an amount of a vacancy and is observed near 365 nm is frequently used as a reference, and a value is also frequently used provided by normalizing an intensity of a yellow luminescence with an intensity of a luminescence at a band edge.

Furthermore, a positron annihilation method has been known as another vacancy evaluation method, although it is not commonly used more than a PL method. A positron annihilation method is a method that irradiates a sample with a positron and detects a gamma ray generated at a time of annihilation of the positron so that a period of time until the annihilation is measured. A period of time for annihilation of a positron is sensitive to a vacancy and its sensitivity greatly depends on a charge of a vacancy. In a case of GaN, only a vacancy of Ga that is a group III element is reflected. The aforementioned two vacancy evaluation methods, that is, both a PL method and a positron annihilation method are sensitive to a vacancy of a group III element, and an evaluation method for a vacancy of N that is a group V element, that is, GaN, has not been established.

Japanese Laid-Open Patent Application No. 2009-147271
Japanese Laid-Open Patent Application No. 2012-089651
Japanese Laid-Open Patent Application No. 2011-027528
Japanese Laid-Open Patent Application No. 2002-280433

SUMMARY

According to an aspect of the embodiments, an analysis device includes an X-ray generation part configured to generate four monochromatic X-rays with different energies to irradiate a sample, an electrically conductive sample stage configured to place the sample thereon and formed of an electrically conductive material, an electrode configured to detect an electric current carried by irradiating the sample with the four monochromatic X-rays with different energies, and an electric power source configured to apply a voltage between the electrically conductive sample stage and the electrode, wherein the four monochromatic X-rays with different energies are X-rays included within a range from an absorption edge of a compound semiconductor included in the sample to a higher energy side of 300 eV.

The object and advantages of the invention will be realized and attained by means of the elements and combinations particularly pointed out in the claims.

It is to be understood that both the forgoing general description and the following detailed description are exemplary and explanatory and are not restrictive of the invention.

BRIEF DESCRIPTION OF THE DRAWING(S)

FIG. 1 is a diagram (1) illustrating an atomic arrangement of a III-V compound semiconductor;

FIG. 2A, FIG. 2B, FIG. 2C, and FIG. 2D are diagrams (2) illustrating atomic arrangements of a III-V compound semiconductor;

FIG. 3 is a structural diagram of an analysis device in a first embodiment;

DESCRIPTION OF EMBODIMENT(S)

Figure 4:
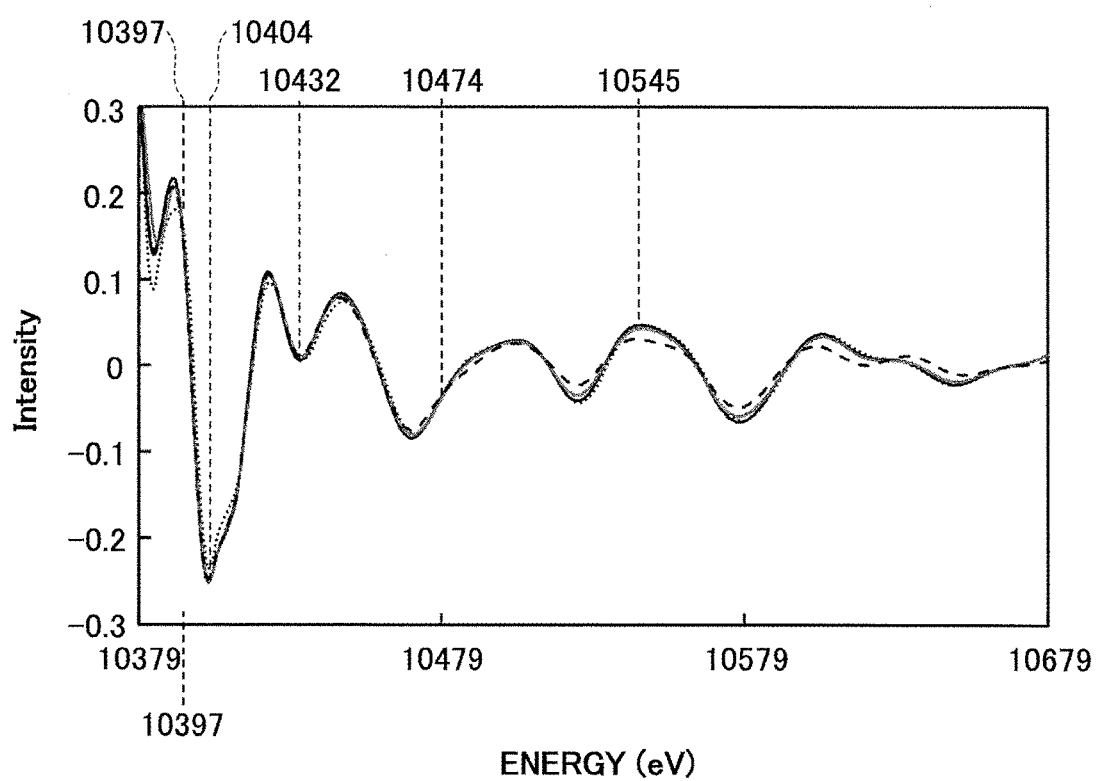
FIG. 4 is a correlation diagram of an energy of an irradiating X-ray and a detected intensity.

Some embodiments for carrying out the invention will be described below. Here, an identical reference numeral will be attached to an identical member or the like and a description(s) thereof will be omitted.

First Embodiment (A Vacancy and a Disturbance of an Atomic Position)

First, a vacancy and a disturbance of an atomic position in a III-V compound semiconductor will be described. FIG. 1 illustrates a state of no vacancy or disturbance of an atomic position in a crystal of a III-V compound semiconductor such as GaN. FIG. 2A, FIG. 2B, FIG. 2C, and FIG. 2D illustrate states of a vacancy or a disturbance of an atomic position caused in a crystal of GaN that is a III-V compound semiconductor. FIG. 2A illustrates a state of a group III element Ga vacancy caused therein and FIG. 2B illustrates a state of a group V element N vacancy caused therein. FIG. 2C illustrates a state of a group III element Ga disturbance caused as a disturbance of an atomic position and FIG. 2D illustrates a state of a group V element N disturbance as a disturbance of an atomic position.

(Analysis Device)

Next, an analysis device in the present embodiment will be described based on FIG. 3. It is possible for an analysis device in the present embodiment to conduct an analysis of a sample 10 formed by, for example, laminating an AlN layer with a thickness of 30 nm and a GaN layer with a thickness of 2 μm on an SiC substrate. An analysis device in the present embodiment has an X-ray source 20, a monochromator 30, a metal foil 40, an electric current amplifiers 51 and 52, V/F converters 61 and 62, an electric power source 70, an electrode 71, an electrically conducive sample stage 72, a scaler 80, a control part 81, and the like. Here, the sample 10 that is an analysis target, the electrode 71, the electrically conductive sample stage 72, and the like are placed in a not-illustrated chamber. Furthermore, an analysis device in the present embodiment is such that an X-ray generation part is formed by the X-ray source 20 and the monochromator 30.

A white X-ray 101 emitted from the X-ray source 20 and having a continuous energy distribution is spectrally dispersed by the monochromator 30. The monochromator 30 may be formed by using, for example, a Ge crystal substrate, an Si crystal substrate, or the like. A spectrally dispersed monochromatic X-ray 102 transmits through the metal foil 40 for monitoring an X-ray intensity. For the metal foil 40, a material difficult to be oxidized is preferable, and for example, a Ni foil or the like that is formed of Ni or the like is preferable. Other than a case where the metal foil 40 is formed by a material difficult to be oxidized, a surface of a metal foil may be coated with a material difficult to be oxidized, and further, the metal foil 40 may be placed in an atmosphere where a removed oxygen or the like is removed.

A thickness of the metal foil 40 is determined by taking an intensity of a transmitted X-ray into consideration. In a case of an energy near a Ga-K absorption edge (E 10~ keV), it is preferable for a thickness of the metal foil 40 to be 0.5 μm-1.5 μm. Here, in a case where a thickness of the metal foil 40 is 0.5 μm, about 92% of an X-ray transmits therethrough, and in a case where a thickness thereof is 1.5 μm, about 77% of an X-ray transmits therethrough. The metal foil 40 is irradiated with the monochromatic X-ray 102 so that an electron escapes from the metal foil 40, and thereby, an electric current flows through the metal foil 40. An electric current flowing through the metal foil 40 is amplified and converted into a voltage by the electric current amplifier 51, and subsequently, converted into a pulse sequence by a V/F converter 61, and a converted pulse sequence is counted by the scaler 80. A result of counting in the scaler 80 is stored in a non-illustrated storage part in a computer for a control and/or analysis that is the control part 81 or the like.

The sample 10 that is an analysis target is placed on the electrically conductive sample stage 72 that doubles as an electrode provided in a non-illustrated chamber and formed of an electrically conductive material such as a metal. The monochromatic X-ray 102 having transmitted through the metal foil 40 irradiates the sample 10 placed on the electrically conductive sample stage 72, and thereby, an electron 110 escapes from the sample 10. Here, a voltage is applied between the electrode 71 and the electrically conductive sample stage 72 that doubles as an electrode by the electric power source 70, and thereby, a voltage is also applied between the sample placed on the electrically conductive sample stage 72 and the electrode 71. An applied voltage is set depending on a distance between the electrode 71 and the electrically conductive sample stage 72 that doubles as an electrode, and for example, in a case where a distance between the electrode 71 and the electrically conductive sample stage 72 is several cm, it is preferable for an applied voltage to be about 1000 V.

In a case where an inside of a non-illustrated chamber is a vacuum, the electron 110 escaping from the sample 10 is attracted at a side of the electrode 71. Furthermore, in a case where an inside of a chamber is filled with an inert gas such as an atmospheric air or helium, a gas to be used for forming a GaN film or the like, or the like, an ion ionized by the escaping electron 110 is attracted at a side of the electrode 71. Thus a flowing electric current is amplified and converted into a voltage by an electric current amplifier 52, and subsequently converted into a pulse sequence by the V/F converter 62. A converted pulse sequence is counted by the scaler 80 and a result of counting by the scaler 80 is stored in a non-illustrated storage part in a computer for control and/or analysis that is the control part 81, or the like.

Here, although a case where the electron 110 escaping from the sample 10 or an ion ionized by the electron 110 escaping from the sample 10 is detected has been described in the above description, an electric current flowing through the sample 10 may be measured directly, similarly to a case of the metal foil 40.

(A Relationship Between an Energy and an Intensity of an X-Ray)

FIG. 4 is a result of a measurement of an intensity detected on the electrode 71 in a case where an energy of an X-ray is changed that irradiates the sample 10 wherein four GaN films are formed with different film formation conditions. An energy value of an X-ray at a left edge of a transverse axis in FIG. 4 is 10379 eV and an energy value of an X-ray at a right edge thereof is 10679 eV, a result of a measurement of an intensity in a range of 300 eV. Here, an energy value of 10379 eV at a left edge of a transverse axis in FIG. 4 corresponds to a value of +11 eV with respect to an energy (10368 eV) at an absorption edge of GaN. Furthermore, as a measurement is further conducted in a higher energy region of an X-ray, it is confirmed that an intensity oscillation as illustrated in FIG. 4 disappears, although it is not illustrated in FIG. 4. Hence, such an intensity oscillation is significant at an energy value of an X-ray in a range of 10379 eV to 10679 eV. Illustrated in FIG. 4 is such that a background curve is obtained based on information in a region with no such intensity oscillation and such background is removed from practical measurement data. For this reason, an intensity oscillation is confirmed centered on an intensity of zero. Here, a difference to be caused by a difference of the sample 10 is not found in a background curve.

As illustrated in FIG. 4, an energy value with a detected intensity difference being greater in a case where samples 10 are different and an energy value with a detected intensity difference being little even when the samples 10 are different are present. Here, it is considered that a Ga vacancy, a N vacancy, a disturbance of an atomic position of Ga, and a disturbance of an atomic position of N are different in different samples 10 and it is supposed that a difference between detected intensities is greater at a certain energy value due to these matters. Here, in the present embodiment, a degree of a disturbance of an atomic position of Ga and a degree of a disturbance of an atomic position of N may be described as a degree of Ga disturbance and a degree of a N disturbance. Here, an analysis device for conducting a measurement while an energy value is changed is not so realistic from the viewpoint of a practicability, because a measurement for obtaining a result as illustrated in FIG. 4 takes about 12 hours for one sample 10.

Meanwhile, an energy value supposed to be sensitive to a Ga vacancy, a N vacancy, a disturbance of an atomic position of Ga, or a disturbance of an atomic position of N is present as described below. Hence, in a case of these energy values, if it is possible to specify which of a Ga vacancy, a N vacancy, a disturbance of an atomic position of Ga, and a disturbance of an atomic position of N an intensity difference is caused by, it is possible to know states of a Ga vacancy, a N vacancy, a disturbance of an atomic position of Ga, and a disturbance of an atomic position of N independently. That is, it is possible to obtain a Ga vacancy, a N vacancy, a disturbance of an atomic position of Ga, and a disturbance of an atomic position of N in a sample 10 independently from intensities obtained by X-rays with four different energy values.

For this reason, what change of an intensity is exhibited at each energy in a case where there is a Ga vacancy, a N vacancy, a disturbance of an atomic position of Ga, or a disturbance of an atomic position of N was calculated by using a non-empirical self-consistent real-space multiple scattering calculation code FEFF that is a kind of a first principle calculation. For a calculation, 182 atoms that were present at distances in 8 angstroms from a target Ga atom were used for analysis and three-or-less-times scattering was taken into consideration for a scattering path. For a crystal structure, a space group $P6_3mc(186)$, a=3.1893 angstroms, and c=5.185 angstroms from PDF#50-0792 were used.

First, calculation of a GaN perfect crystal with no vacancy or disturbance of an atomic position as illustrated in FIG. 1 was conducted. Then, a calculation was conducted for a case where there is a vacancy or a disturbance as illustrated in FIG. 2A, FIG. 2B, FIG. 2C, and FIG. 2D. In a case of a Ga vacancy as illustrated in FIG. 2A, a calculation was first conducted for a state that one Ga atom was not present. First, each vacancy was calculated for all of Ga atoms in 8 angstroms and an average value thereof was calculated. Then, a state was calculated that two Ga atoms were not present. Two Ga atoms are selected randomly and a calculation was conducted for vacancies thereof. A calculation was conducted repeatedly for a state that there were vacancies of two Ga atoms and an average value thereof was calculated. A selection of an atom(s), a calculation, and a calculation of an average value were conducted repeatedly until the average value was converged. Similarly, a state that three Ga atoms were not present, a state that four Ga atoms were not present, and a state that there were more vacancies were calculated to obtain a relationship between a rate of vacancy and an intensity. A calculation similar to a case of Ga was also conducted for a case of a N vacancy illustrated in FIG. 2B.

For a disturbance of an atomic position, a calculation was conducted while a magnitude of a Debye-Waller factor was changed. For each of a Ga atom and a N atom, cases where Debye-Waller factors were different were calculated to obtain a relationship between a disturbance of each atomic position and an intensity. In an actual measurement, the above-mentioned relationship was researched for each 1 eV with respect to an energy with a greatly changed intensity due to a difference between the samples 10. In many energies, there was a dependency on all of four parameters that were a Ga vacancy, a N vacancy, a disturbance of an atomic position of Ga, and a disturbance of an atomic position of N, and only a degree of the dependency was different. If a dependency was identical for all energies, it is not possible to calculate the above-mentioned four parameters.

However, it was possible to find five energy values having features in the dependency, that is, 10397 eV, 10404 eV, 10545 eV, 10474 eV, and 10432 eV, from a result of a measurement and a result of calculation in the above description. The present embodiment was provided based on thus found observation.

(Analysis Method)

Next, a relationship between a rate of vacancy or a disturbance of an atomic position and an intensity at five energy values that exhibit characteristic trends on these dependencies, that is, 10397 eV, 10404 eV, 10545 eV, 10474 eV, and 10432 eV, will be described.

Figure 5A:
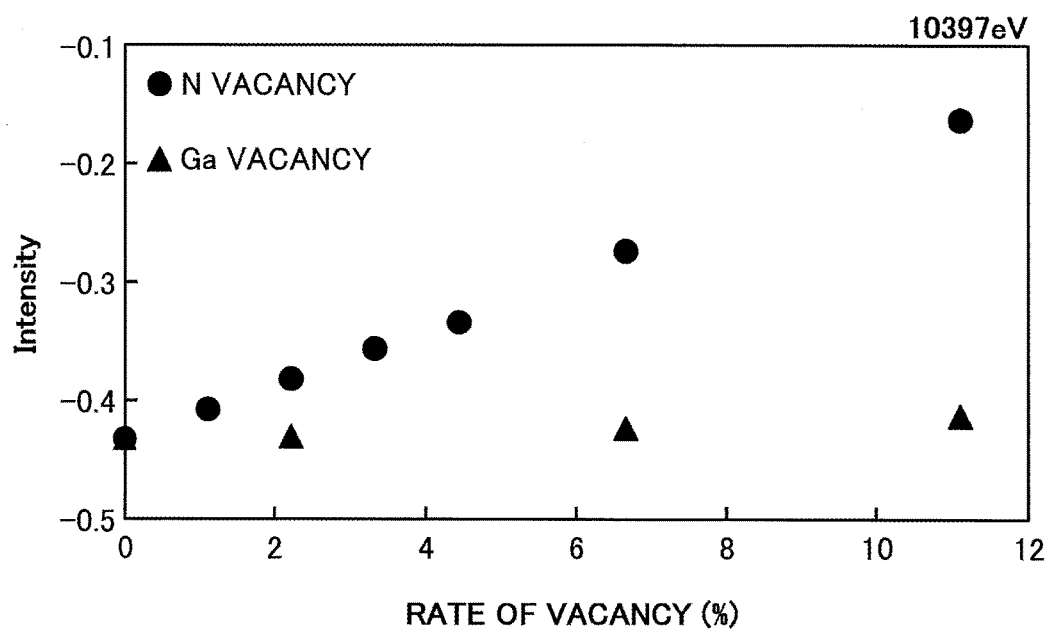
FIG. 5A and FIG. 5B are diagrams illustrating a vacancy and a disturbance of an atomic position in a case where an energy of an X-ray is 10397 eV.
Figure 5B:
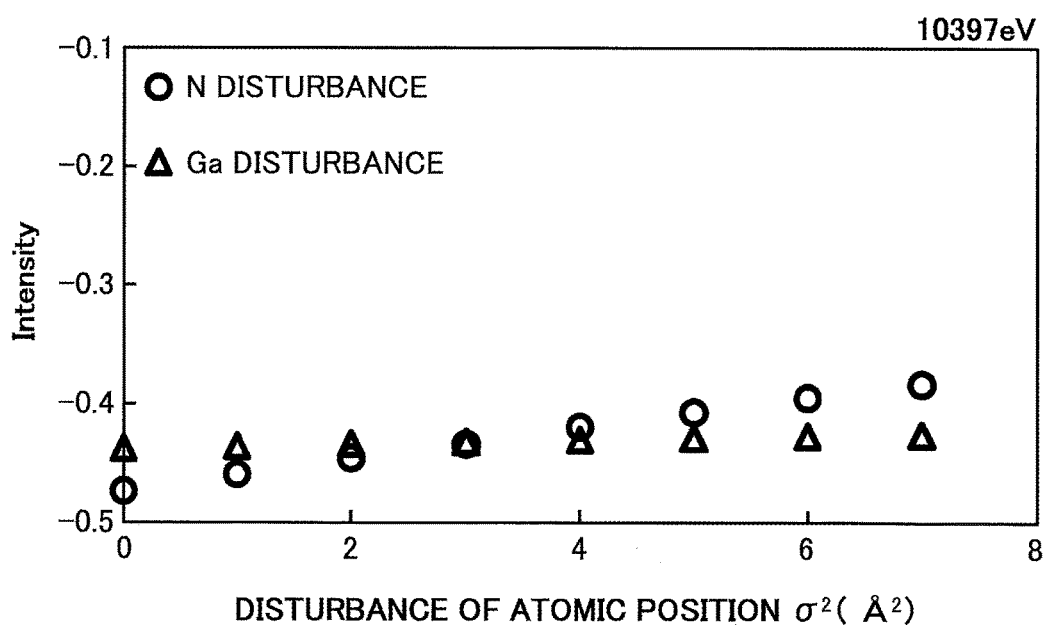

FIG. 5A and FIG. 5B illustrate a relationship between a rate of vacancy or a disturbance of an atomic position and an intensity in a case where an energy value of an X-ray is 10397 eV. FIG. 5A illustrates a relationship between a rate of vacancy and an intensity and FIG. 5B illustrates a relationship between a disturbance of an atomic position and an intensity. As illustrates in FIG. 5A and FIG. 5B, an intensity is hardly changed for a Ga vacancy and an intensity is changed depending on a rate of vacancy for an N vacancy, in a case where an energy value of an X-ray is 10397 eV. Furthermore, for a disturbance of an atomic position, an intensity is hardly changed for each of a Ga disturbance and a N disturbance. Therefore, it is possible to measure a rate of vacancy for an N vacancy by only conducting a measurement in a case where an energy value of an X-ray is 10397 eV.

Figure 6A:
FIG. 6A and FIG. 6B are diagrams illustrating a vacancy and a disturbance of an atomic position in a case where an energy of an X-ray is 10404 eV.
Figure 6B:
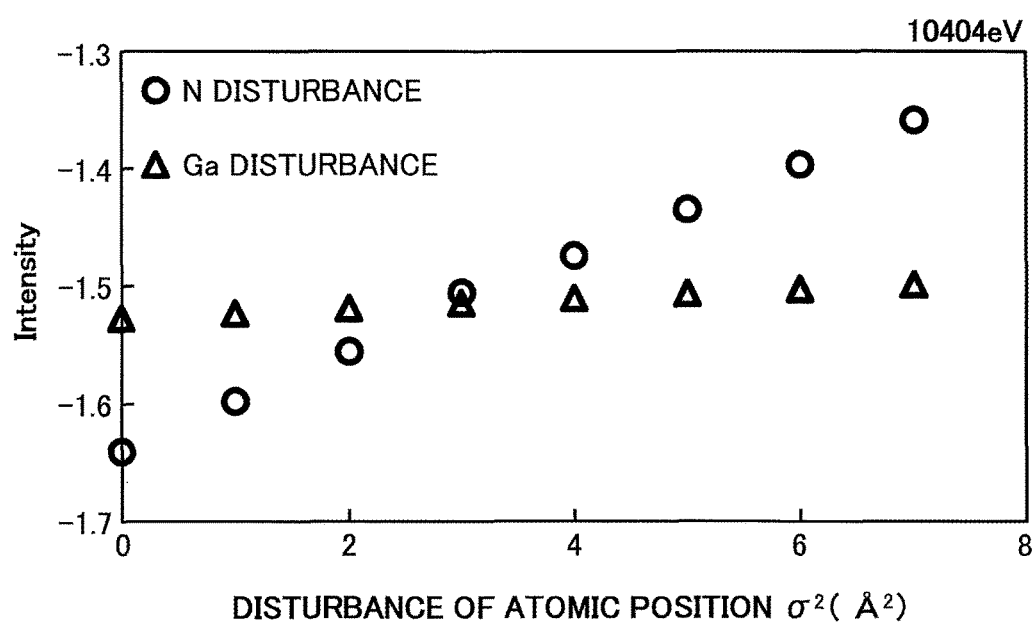

FIG. 6A and FIG. 6B illustrate a relationship between a rate of vacancy or a disturbance of an atomic position and an intensity in a case where an energy value of an X-ray is 10404 eV. FIG. 6A illustrates a relationship between a rate of vacancy and an intensity and FIG. 6B illustrates a relationship between a disturbance of an atomic position and an intensity. As illustrates in FIG. 6A and FIG. 6B, an intensity is hardly changed for a Ga vacancy and an intensity is changed depending on a rate of vacancy for an N vacancy, in a case where an energy value of an X-ray is 10404 eV. Furthermore, for a disturbance of an atomic position, an intensity is hardly changed for a Ga disturbance and an intensity is changed depending on a degree of a disturbance of an atomic position for an N disturbance. Thus, an intensity is changed depending on a rate of vacancy for an N vacancy or a degree of an N disturbance in a case where an energy value of an X-ray is 10404 eV. Therefore, it is possible to calculate a degree of a N disturbance by conducting a measurement in a case where an energy value of an X-ray is 10404 eV and taking into consideration a measurement in a case where an energy value of an X-ray is 10397 eV, that is, a rate of vacancy for an N vacancy.

Figure 7A:
FIG. 7A and FIG. 7B are diagrams illustrating a vacancy and a disturbance of an atomic position in a case where an energy of an X-ray is 10545 eV.
Figure 7B:
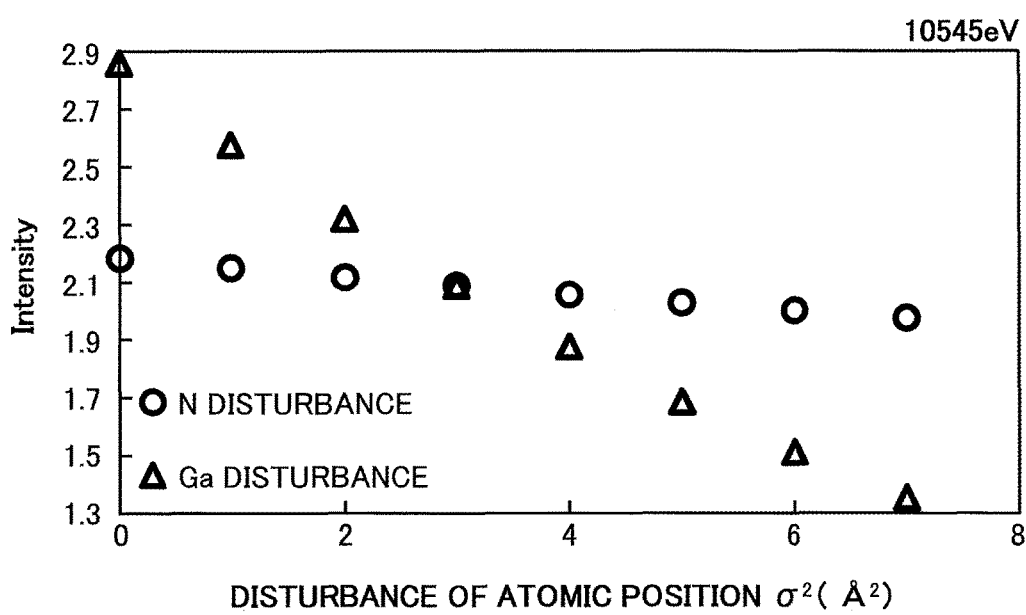

FIG. 7A and FIG. 7B illustrate a relationship between a rate of vacancy or a disturbance of an atomic position and an intensity in a case where an energy value of an X-ray is 10545 eV. FIG. 7A illustrates a relationship between a rate of vacancy and an intensity and FIG. 7B illustrates a relationship between a disturbance of an atomic position and an intensity. As illustrates in FIG. 7A and FIG. 7B, an intensity is hardly changed for a Ga vacancy or a N vacancy in a case where an energy value of an X-ray is 10545 eV. Furthermore, for a disturbance of an atomic position, an intensity is changed depending on a degree of a disturbance of an atomic position for a Ga disturbance and an intensity is hardly changed for an N disturbance. Therefore, it is possible to measure a degree of a disturbance of an atomic position for Ga by conducting only a measurement in a case where an energy value of an X-ray is 10545 eV.

Figure 8A:
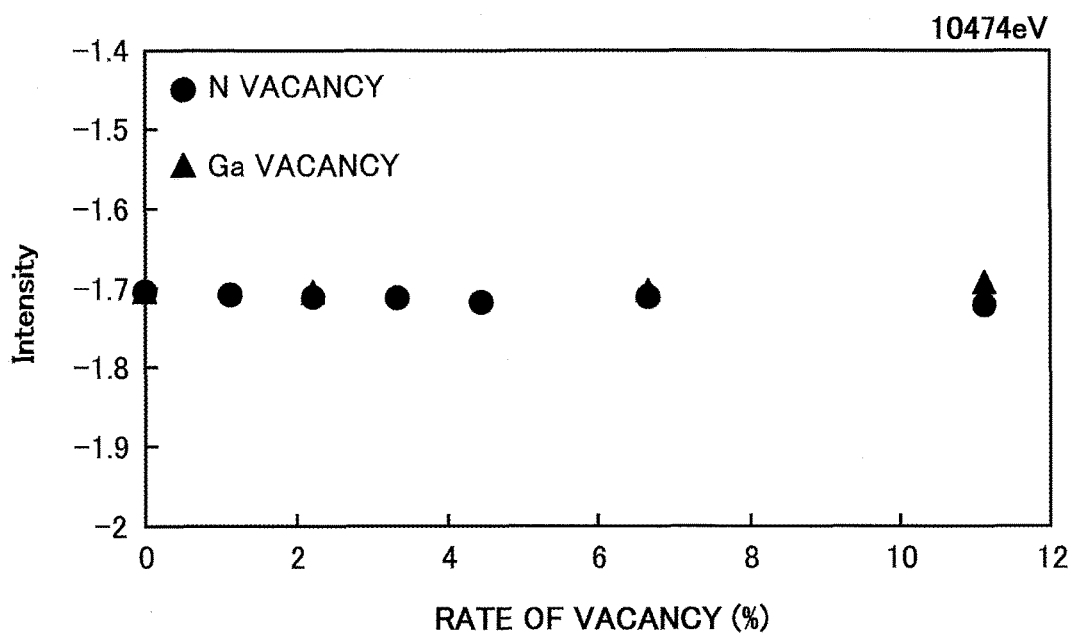
FIG. 8A and FIG. 8B are diagrams illustrating a vacancy and a disturbance of an atomic position in a case where an energy of an X-ray is 10474 eV.
Figure 8B:
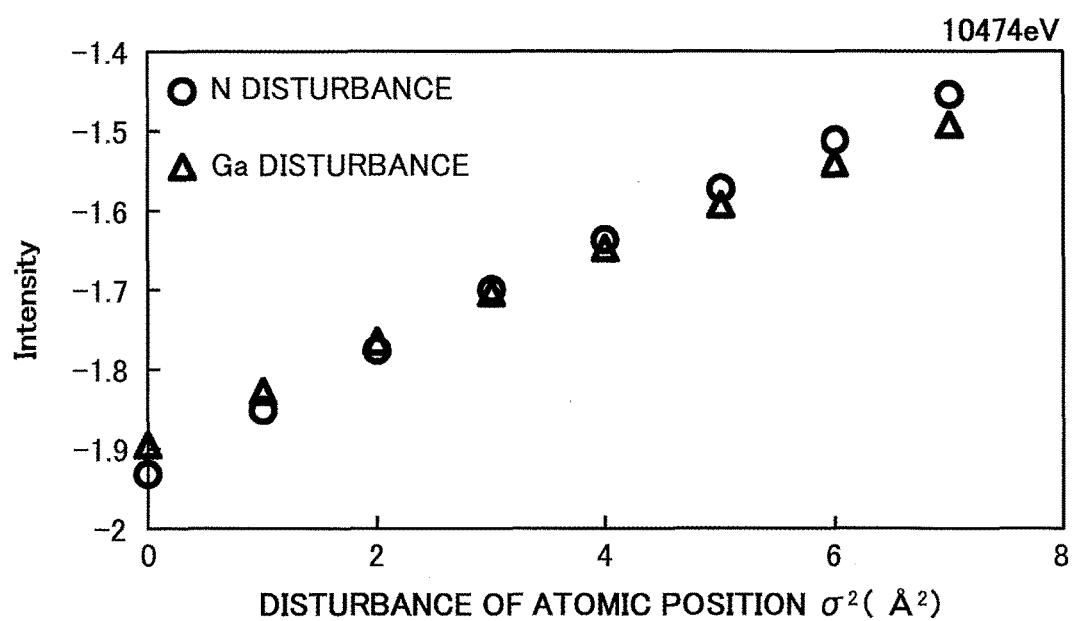

FIG. 8A and FIG. 8B illustrate a relationship between a rate of vacancy or a disturbance of an atomic position and an intensity in a case where an energy value of an X-ray is 10474 eV. FIG. 8A illustrates a relationship between a rate of vacancy and an intensity and FIG. 8B illustrates a relationship between a disturbance of an atomic position and an intensity. As illustrates in FIG. 8A and FIG. 8B, an intensity is hardly changed for a Ga vacancy or a N vacancy in a case where an energy value of an X-ray is 10474 eV. Furthermore, for a disturbance of an atomic position, an intensity is changed depending on a degree of a disturbance of an atomic position for a Ga disturbance or an N disturbance. Thus, an intensity is changed depending on a degree of a Ga disturbance or an N disturbance in a case where an energy value of an X-ray is 10474 eV. Therefore, it is possible to calculate a degree of a N disturbance by conducting a measurement in a case where an energy value of an X-ray is 10474 eV and taking into consideration a measurement in a case where an energy value of an X-ray is 10545 eV, that is, a degree of a disturbance of an atomic position of Ga.

Figure 9A:
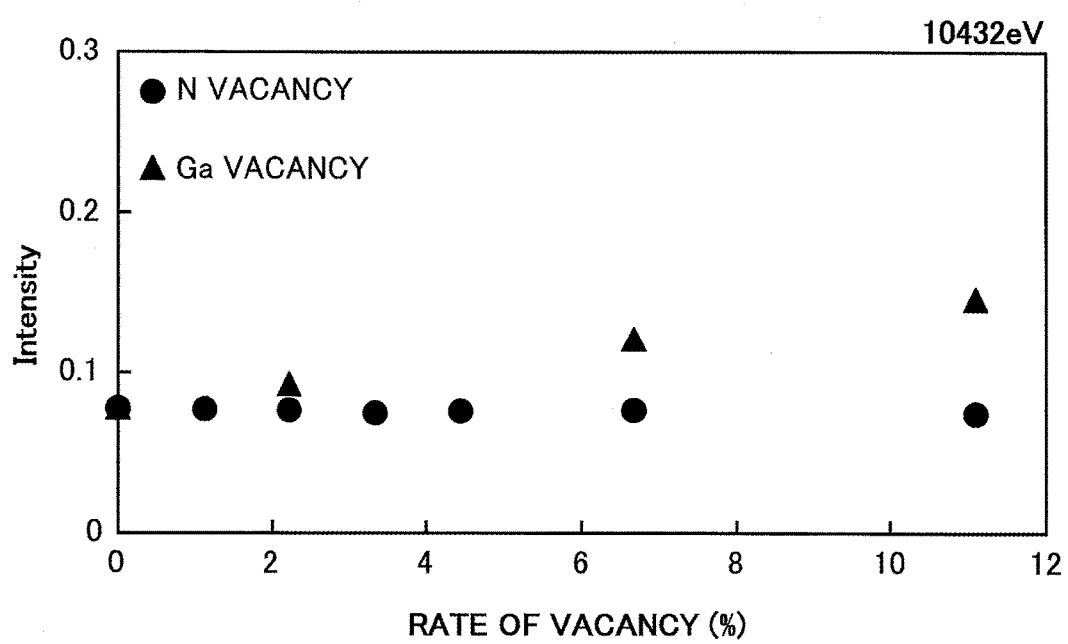
FIG. 9A and FIG. 9B are diagrams illustrating a vacancy and a disturbance of an atomic position in a case where an energy of an X-ray is 10432 eV.
Figure 9B:
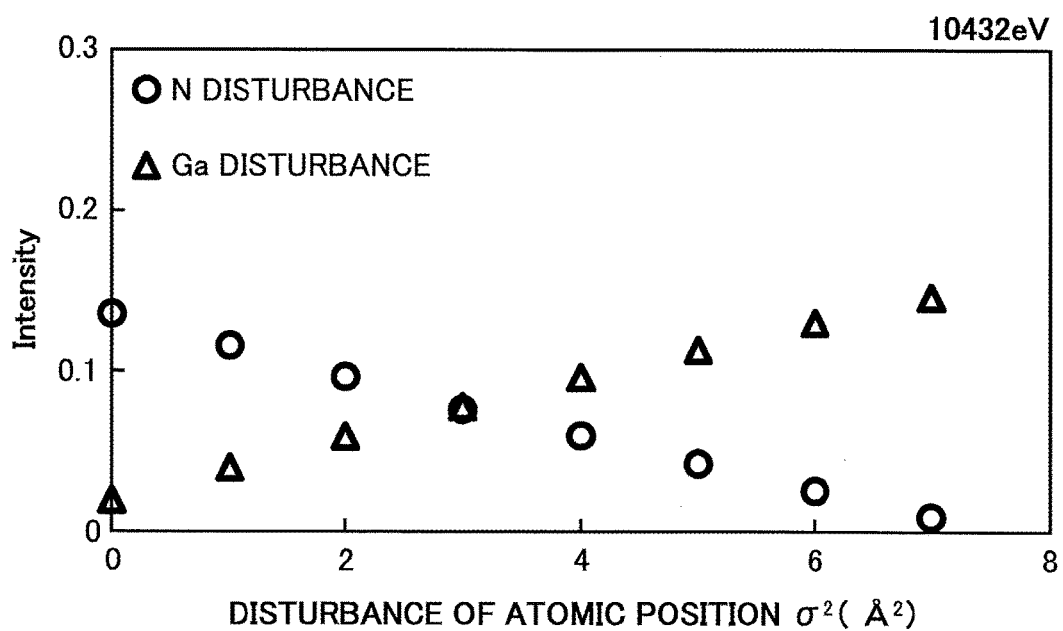

FIG. 9A and FIG. 9B illustrate a relationship between a rate of vacancy or a disturbance of an atomic position and an intensity in a case where an energy value of an X-ray is 10432 eV. FIG. 9A illustrates a relationship between a rate of vacancy and an intensity and FIG. 9B illustrates a relationship between a disturbance of an atomic position and an intensity. As illustrates in FIG. 9A and FIG. 9B, an intensity is changed depending on a rate of vacancy for a Ga vacancy and an intensity is hardly changed for a N vacancy in a case where an energy value of an X-ray is 10432 eV. Furthermore, for a disturbance of an atomic position, an intensity is changed depending on a degree of a disturbance of an atomic position for a Ga disturbance or an N disturbance. Thus, an intensity is changed depending on a rate of vacancy for a Ga vacancy or degree of a Ga distribution or N distribution in a case where an energy value of an X-ray is 10432 eV. Hence, it is possible to calculate a rate of vacancy for a Ga vacancy by conducting a measurement in a case where an energy value of an X-ray is 10432 eV and taking into consideration results of measurements in a case where energy values of X-rays are 10545 eV and 10474 eV. Alternatively, it is possible to calculate a rate of vacancy for a Ga vacancy by conducting a measurement in a case where an energy value of an X-ray is 10432 eV and taking into consideration results of measurements in a case where energy values of X-rays are 10545 eV and 10404 eV.

As described above, it is possible to derive four parameters that are a Ga vacancy, an N vacancy, a disturbance of an atomic position of Ga, and a disturbance of an atomic position of N by conducting measurements at four different energies.

Figure 10:
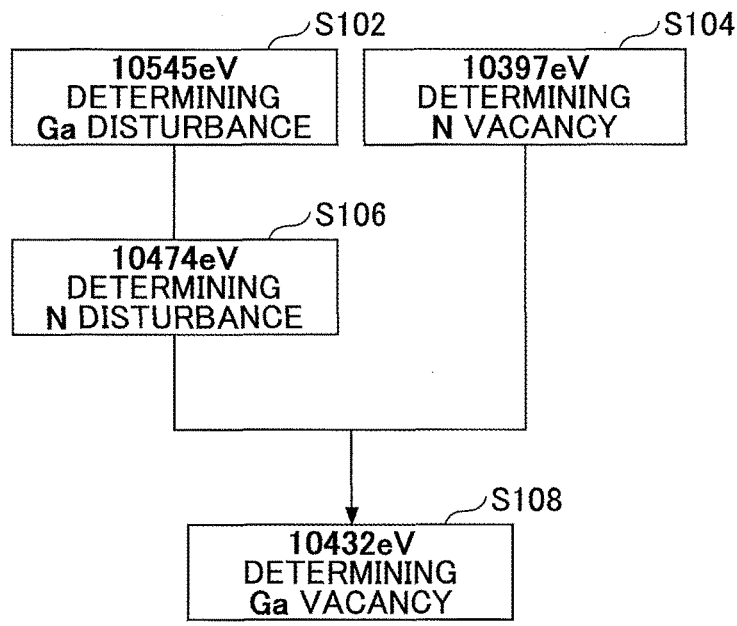
FIG. 10 is a diagram (1) illustrating an analysis method in the first embodiment.
Figure 11:
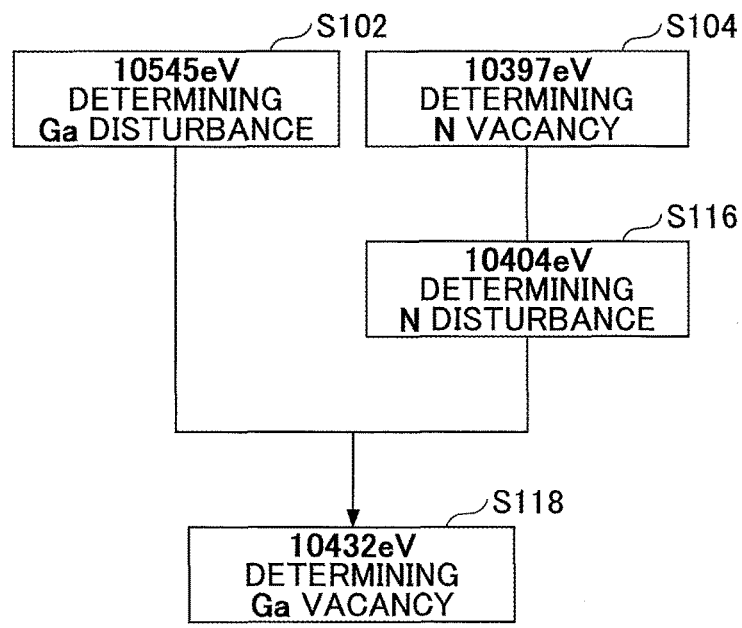
FIG. 11 is a diagram (2) illustrating an analysis method in the first embodiment.

For a pattern in an analysis method in the present embodiment, it is possible to consider two kinds that are a pattern illustrated in FIG. 10 and a pattern illustrated in FIG. 11.

In a pattern illustrated in FIG. 10, first, the sample 10 is placed on the electrically conductive sample stage 72, and subsequently, a voltage is applied between the electrically conductive sample stage 72 and the electrode 71 by the electric power source 70. After that, step 102 (S102) and step 104 (S104) are conducted, then step 106 (S106) is conducted, and subsequently, step 108 (S108) is conducted.

At S102, a degree of a disturbance of an atomic position of Ga is measured based on a measurement result measured in a case where an energy value of an X-ray is 10545 eV.

At S104, a rate of vacancy for an N vacancy is measured based on a measurement result measured in a case where an energy value of an X-ray is 10397 eV.

At S106, a degree of a disturbance of an atomic position of N is calculated based on a measurement result measured in a case where an energy value of an X-ray is 10474 eV and a measurement result measured in a case of 10545 eV.

At S108, a rate of vacancy for a Ga vacancy is calculated based on a measurement result measured in a case where an energy value of an X-ray is 10432 eV and measurement results measured in cases of 10545 eV and 10474 eV.

In a pattern illustrated in FIG. 11, first, the sample 10 is placed on the electrically conductive sample stage 72, and subsequently, a voltage is applied between the electrically conductive sample stage 72 and the electrode 71 by the electric power source 70. After that, step 102 (S102) and step 104 (S104) are conducted, then step 116 (S11406) is conducted, and subsequently, step 118 (S118) is conducted.

At S102, a degree of a disturbance of an atomic position of Ga is measured based on a measurement result measured in a case where an energy value of an X-ray is 10545 eV.

At S104, a rate of vacancy for an N vacancy is measured based on a measurement result measured in a case where an energy value of an X-ray is 10397 eV.

At S116, a degree of a disturbance of an atomic position of N is calculated based on a measurement result measured in a case where an energy value of an X-ray is 10404 eV and a measurement result measured in a case of 10397 eV.

At S118, a rate of vacancy for a Ga vacancy is calculated based on a measurement result measured in a case where an energy value of an X-ray is 10432 eV and measurement results measured in cases of 10545 eV, 10397 eV, and 10404 eV.

Thus, it is possible to conduct an analysis more efficiently by conducting a pattern illustrated in FIG. 10 or a pattern illustrated in FIG. 11.

Here, in a case where the above-mentioned energy value of an X-ray is 10397 eV, an energy value of an X-ray may be 10392 eV or greater and 10402 eV or less, and more preferably may be 10394 eV or greater and 10400 eV or less. Moreover, 10396 eV or greater and 10398 eV or less is more preferable.

Furthermore, in a case where the above-mentioned energy value of an X-ray is 10404 eV, an energy value of an X-ray may be 10399 eV or greater and 10409 eV or less, and more preferably may be 10401 eV or greater and 10407 eV or less. Moreover, 10403 eV or greater and 10405 eV or less is more preferable.

Furthermore, in a case where the above-mentioned energy value of an X-ray is 10545 eV, an energy value of an X-ray may be 10540 eV or greater and 10550 eV or less, and more preferably may be 10542 eV or greater and 10548 eV or less. Moreover, 10544 eV or greater and 10546 eV or less is more preferable.

Furthermore, in a case where the above-mentioned energy value of an X-ray is 10474 eV, an energy value of an X-ray may be 10469 eV or greater and 10479 eV or less, and more preferably may be 10471 eV or greater and 10477 eV or less. Moreover, 10473 eV or greater and 10475 eV or less is more preferable.

Furthermore, in a case where the above-mentioned energy value of an X-ray is 10432 eV, an energy value of an X-ray may be 10427 eV or greater and 10437 eV or less, and more preferably may be 10429 eV or greater and 10435 eV or less. Moreover, 10431 eV or greater and 10433 eV or less is more preferable.

(A Structure of an Analysis Device)

Figure 12:
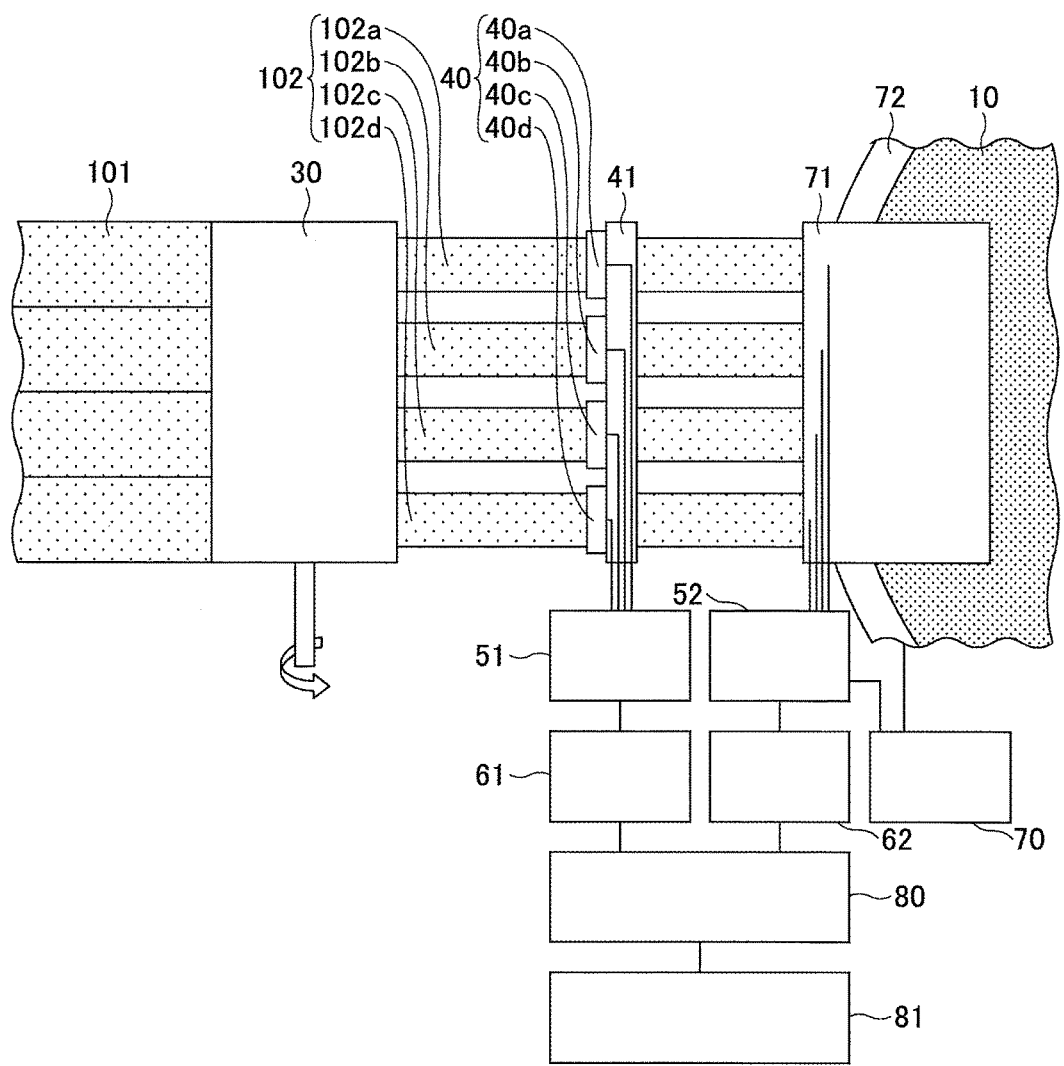
FIG. 12 is a diagram (1) illustrating an analysis device in the first embodiment.
Figure 13A:
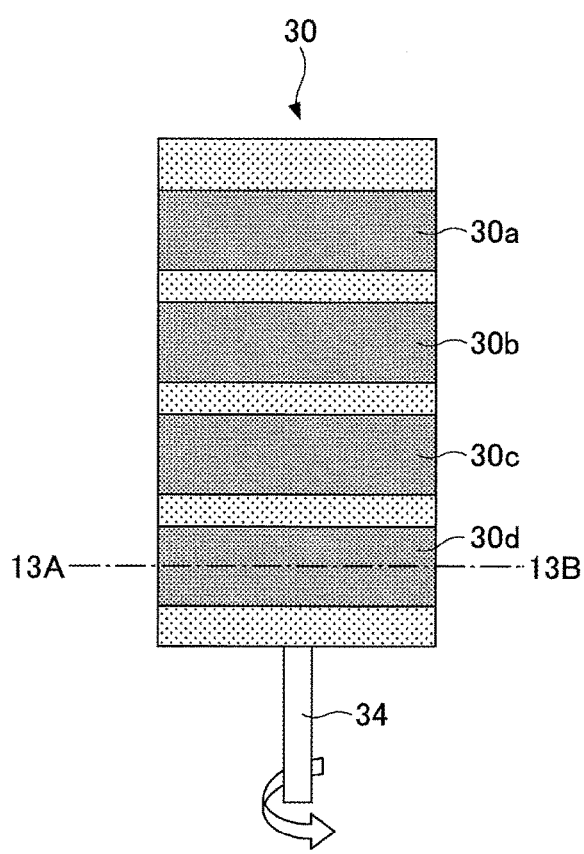
FIG. 13A and FIG. 13B are diagrams (2) illustrating an analysis device in the first embodiment.
Figure 13B:
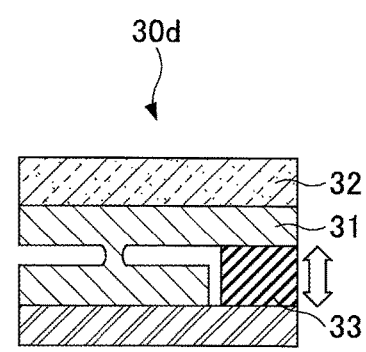

An analysis device in the present embodiment is such that a white X-ray 101 is spectrally dispersed by the monochromator 30 as illustrated in FIG. 12. As illustrated in FIG. 13A and FIG. 13B, the monochromator 30 has a monochromator body part 31 and four Ge substrates for forming four independent monochromatic function parts are placed at a side of irradiation with the white X-ray 101 in the monochromator body part 31. Each of a first monochromatic function part 30a, a second monochromatic function part 30b, a third monochromatic function part 30c, and a fourth monochromatic function part 30d is provided with a Ge substrate 32, and further, a piezoelectric element 33 capable of adjusting an angle of the Ge substrate finely is mounted thereon. Here, FIG. 13A illustrates the monochromator 30 when viewed from a side of irradiation with the white X-ray 101 and FIG. 13B is a cross-sectional view as being cut along a dashed-dotted line 13A-13B in FIG. 13A. Although FIG. 13B illustrates a cross-sectional structure of the fourth monochromatic function part 30d, the first monochromatic function part 30a, the second function part 30b, and the third monochromatic function part 30c also have a similar structure.

Furthermore, the monochromator 30 is formed in such a manner that it is possible to select an X-ray with a desired energy value by being centrally rotated on a rotation axis 34. For example, in a case where it is desired that analysis for GaN is conducted, it is possible to adjust an X-ray reflected in the monochromator 30 to have an energy value near about 10368 eV that is a Ga—K absorption edge by being centrally rotated on the rotation axis 34.

The piezoelectric element 33 is formed of a ferroelectric substance such as $Pb(Zr,Ti)O_3$ and stretched or displaced by applying a voltage thereto, wherein it is possible to finely adjust an amount of displacement depending on an applied voltage. Each of four monochromatic function parts in the monochromator 30, namely, the first monochromatic function part 30a, the second monochromatic function part 30b, the monochromatic function part 30c, and the fourth monochromatic function part 30d is provided with such a piezoelectric element 33. Thereby, it is possible to independently change an angle of a white X-ray 101 incident on four monochromatic function parts in the monochromator 30, namely, the first monochromatic function part 30a, the second monochromatic function part 30b, the monochromatic function part 30c, and the fourth monochromatic function part 30d. That is, it is possible to obtain four monochromatic X-rays 102a, 102b, 102c, and 102d with different energies near 10368 eV by the first monochromatic function part 30a, the second monochromatic function part 30b, the monochromatic function part 30c, and the fourth monochromatic function part 30d.

Therefore, it is possible to obtain a first monochromatic X-ray 102a due to the first monochromatic function part 30a, a second monochromatic X-ray 102b due to the second monochromatic function part 30b, a third monochromatic X-ray 102c due to the third monochromatic function part 30c, and a fourth monochromatic X-ray 102d due to the fourth monochromatic function part 30d. Here, the first monochromatic X-ray 102a, the second monochromatic X-ray 102b, the third monochromatic X-ray 102c, and the fourth monochromatic X-ray 102d are monochromatic X-rays with mutually different energies.

These four monochromatic X-rays with different energies, namely, the first monochromatic X-ray 102a, the second monochromatic X-ray 102b, the third monochromatic X-ray 102c, and the fourth monochromatic X-ray 102d are first incident on the metal foil 40. The metal foil 40 is formed in such a manner that four windows are formed on a substrate 41 formed of an insulator and each of the four windows is provided with a metal foil, as a first metal foil part 40a, a second metal foil part 40b, a third metal foil part 40c, and a fourth metal foil part 40d. The first metal foil part 40a, the second metal foil part 40b, the third metal foil part 40c, and the fourth metal foil part 40d are mutually electrically insulated.

The first monochromatic X-ray 102a caused to be monochromatic by the first monochromatic function part 30a is incident on the first metal foil part 40a so that an electric current flows through the first metal foil part 40a. An electric current flowing through the first metal foil part 40a is amplified and converted into a voltage by the electric current amplifier 51, and subsequently converted into a pulse sequence by the V/F converter 61, and a converted pulse sequence is counted by the scaler 80.

Furthermore, the second monochromatic X-ray 102b caused to be monochromatic by the second monochromatic function part 30b is incident on the second metal foil part 40b so that an electric current flows through the second metal foil part 40b. An electric current flowing through the second metal foil part 40b is amplified and converted into a voltage by the electric current amplifier 51, and subsequently converted into a pulse sequence by the V/F converter 61, and a converted pulse sequence is counted by the scaler 80.

Furthermore, the third monochromatic X-ray 102c caused to be monochromatic by the third monochromatic function part 30c is incident on the third metal foil part 40c so that an electric current flows through the third metal foil part 40c. An electric current flowing through the third metal foil part 40c is amplified and converted into a voltage by the electric current amplifier 51, and subsequently converted into a pulse sequence by the V/F converter 61, and a converted pulse sequence is counted by the scaler 80.

Furthermore, the fourth monochromatic X-ray 102d caused to be monochromatic by the fourth monochromatic function part 30d is incident on the fourth metal foil part 40d so that an electric current flows through the fourth metal foil part 40d. An electric current flowing through the fourth metal foil part 40d is amplified and converted into a voltage by the electric current amplifier 51, and subsequently converted into a pulse sequence by the V/F converter 61, and a converted pulse sequence is counted by the scaler 80.

Thus, a result of counting by the scaler 80 is stored in a non-illustrated storage part in a computer for a control and an analysis or the like that is the control part 81.

The first monochromatic X-ray 102a transmitted through the first metal foil part 40a, the second monochromatic X-ray 102b transmitted through the second metal foil part 40b, the third monochromatic X-ray 102c transmitted through the third metal foil part 40c, and the fourth monochromatic X-ray 102d transmitted through the fourth metal foil part 40d irradiate the sample 10. The sample 10 is irradiated with the first monochromatic X-ray 102a, the second monochromatic X-ray 102b, the third monochromatic X-ray 102c, and the fourth monochromatic X-ray 102d so that the electron 110 escapes from the sample 10 and the escaping electron 110 is attracted by the electrode 71.

Figure 14A:
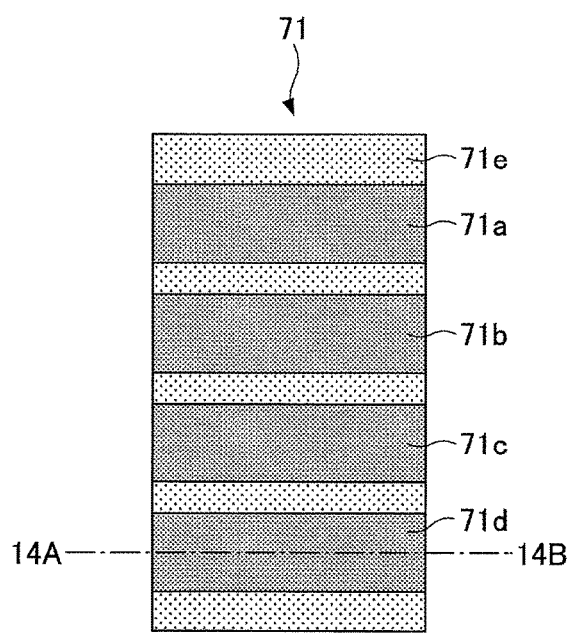
FIG. 14A and FIG. 14B are diagrams (3) illustrating an analysis device in the first embodiment.
Figure 14B:
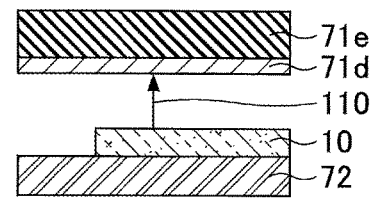

As illustrated in FIG. 14A and FIG. 14B, the electrode 71 is such that four independent electrodes, namely, a first electrode 71a, a second electrode 71b, a third electrode 71c, and a fourth electrode 71d, are formed on a substrate 71e formed of an insulator. The first electrode 71a, the second electrode 71b, the third electrode 71c, and the fourth electrode 71d are mutually insulated. Here, FIG. 14A illustrates a structure of the electrode 71 when viewed from a side of the sample 10 and FIG. 14B is a cross-sectional view as being cut along a dashed-dotted line 14A-14B in FIG. 14A. Although FIG. 14B illustrates a cross-sectional structure of the fourth electrode 71d, the first electrode 71a, the second electrode 71b, and the third electrode 71c also have a similar structure.

In the present embodiment, it is possible for the first electrode 71a to detect an electric current flown by irradiating the sample 10 with the first monochromatic X-ray 102a. It is possible for the second electrode 71b to detect an electric current flown by irradiating the sample 10 with the second monochromatic X-ray 102b. It is possible for the third electrode 71c to detect an electric current flown by irradiating the sample 10 with the third monochromatic X-ray 102c. It is possible for the fourth electrode 71d to detect an electric current flown by irradiating the sample 10 with the fourth monochromatic X-ray 102d.

Thus, it is possible for the electrode 71 to independently measure an electric current flown by irradiating the sample 10 with each of the first monochromatic X-ray 102a, the second monochromatic X-ray 102b, the third monochromatic X-ray 10ca, and the fourth monochromatic X-ray 102d. Therefore, an electric current flown by the electron 110 or an anion that escapes from the sample 10 is amplified and converted into a voltage by an electric current amplifier 52, and subsequently, converted into a pulse sequence by the V/F converter 62, and each converted pulse sequence is independently counted by the scaler 80. A result of counting by the scaler 80 is stored in a non-illustrated storage part in a computer for a control and an analysis or the like that is the control part 81. It is possible for the control part 81 to calculate a Ga vacancy, a N vacancy, a disturbance of an atomic position of Ga, and a disturbance of an atomic position of N based on information stored in a non-illustrated storage part.

Second Embodiment (A Film Formation Device and a Film Formation Method)

Next, a second embodiment will be described. The present embodiment is a film formation device that includes an analysis device in the first embodiment and a film formation method that uses an analysis method in the first embodiment.

Figure 15:
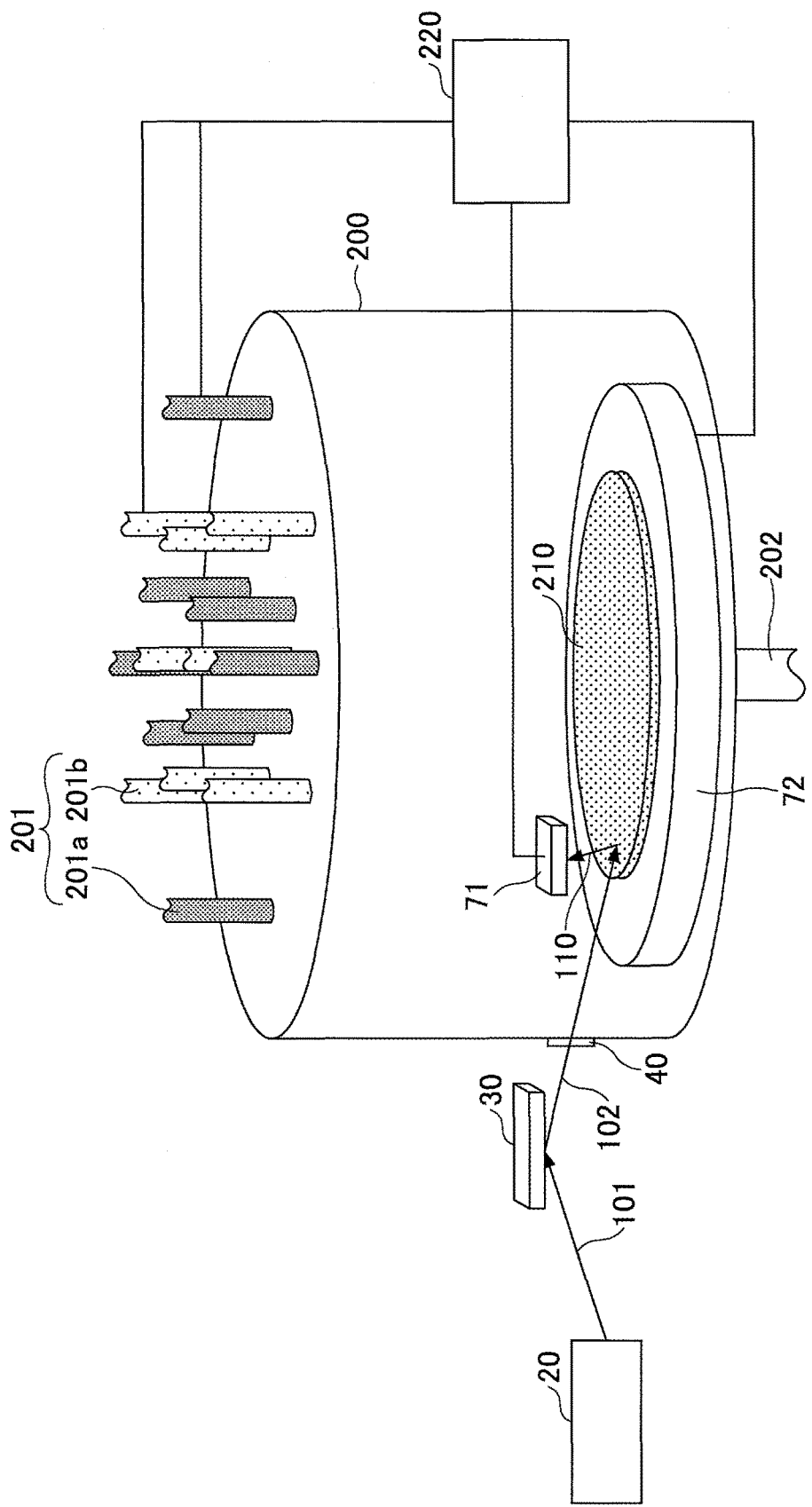
FIG. 15 is a structural diagram of a film formation device in a second embodiment.

A film formation device in the present embodiment will be described based on FIG. 15. A film formation device illustrated in FIG. 15 is a so-called vertical type Metal-Organic Chemical Vapor Deposition (MOCVD) film formation device.

In a film formation device in the present embodiment, the white X-ray 101 emitted from the X-ray source 20 and having a continuous energy distribution is spectrally dispersed into the monochromatic X-ray 102 by the monochromator 30 and transmits through the metal foil 40 for monitoring an X-ray intensity. The monochromatic X-ray 102 transmits through the metal foil 40 so that an electron escapes from the metal foil 40 and thereby an electric current flows through the metal foil 40. An electric current flowing through the metal foil 40 is amplified and converted into a voltage by an electric current amplifier that is not illustrated in FIG. 15 and subsequently converted into a pulse sequence by a V/F converter, and a converted pulse sequence is counted by a scaler. A result of counting by a scaler is stored in a computer for a control and an analysis that is a control part.

In a film formation device in the present embodiment, the electrically conductive sample stage 72 and the electrode 71 are placed in a film formation chamber 200 and a voltage with predetermined value is applied between the electrically conductive sample stage 72 and the electrode 71. The monochromatic X-ray 102 having transmitted through the metal foil 40 irradiates a sample 210 that is placed on the electrically conductive sample stage 72 doubling as an electrode placed in the chamber 200 and is a film formation target. Thereby, the electron 110 escapes from the sample 210. The electron 110 escapes from the sample 210 by irradiation with the monochromatic X-ray 102 or a gas in the film formation chamber 200 is ionized by the escaping electron 110, so that an electric current flows through the electrode 71. An electric current flowing through the electrode 71 is amplified and converted into a voltage by an electric current amplifier and converted into a pulse sequence by a V/F converter and a converted pulse sequence is counted by a scaler. A result of counting by a scaler is stored in a computer for a control and an analysis that is a control part.

An analysis on, for example, a pattern illustrated in FIG. 10 or an pattern illustrated in FIG. 11 is conducted based on a result of a measurement stored in a control part, so that rates of vacancy for an N vacancy and a Ga vacancy and a degrees of an N disturbance and a Ga disturbance are derived. A feedback is applied to a fabrication condition based on thus derived rates of vacancy for an N vacancy and a Ga vacancy and degrees of an N disturbance and a Ga disturbance.

Here, the sample 210 is conveyed by using a non-illustrated transfer robot to be placed on the electrically conductive sample stage 72. A non-illustrated heater part having a heater function to be capable of heating the sample 210 is installed in the electrically conductive sample stage 72 doubling as an electrode and plays a role of a so-called "susceptor". A susceptor is provided with a non-illustrated rotation mechanism part capable of rotating the sample 210 in order to improve a uniformity of a film formed on the sample 210. Here, although a case of one electrically conductive sample stage 72 is illustrated in FIG. 15, a plurality of electrically conductive sample stages 72 may be provided. Furthermore, in a case of a plurality of electrically conductive sample stages 72, a non-illustrated revolution mechanism part may be provided that is capable of changing positions of the electrically conductive sample stages 72.

It is possible to conduct an introduction of a raw material gas and a carrier gas into the film formation chamber 200 at a gas introduction port 201 and conduct exhaust thereof at a gas exhaust port 202. In a film formation device in the present embodiment, a group III raw material gas is introduced by using a gas introduction port 201a and a group V raw material gas is introduced by using a gas introduction port 201b, so that the group III raw material gas and the group V raw material gas are separately introduced into the film formation chamber 200. Thereby, it is possible to control a gas phase reaction in the film formation chamber 200.

In the present embodiment, it is possible to use $N_2$, $H_2$, a mixed gas of $N_2$ and $H_2$, or the like as a carrier gas that is introduced together with a group III raw material gas and a group V raw material gas. Furthermore, in regard to a raw material gas to be introduced, in a case where a GaN film is formed, trimethylgallium (TMG), triethylgallium (TEG), or the like is used as a group III raw material gas. Furthermore, ammonia ($NH_3$), dimethylhydrazine (DMHy), or the like is used as a group V raw material gas.

Furthermore, in a case where an aluminum nitride (AlN) film is formed, trimethylaluminum (TMA), triethylaluminum (TEA), tri(tertiary butyl)aluminum (TTBA), or the like is used as a group III raw material gas. Furthermore, ammonia ($NH_3$), dimethylhydrazine (DMHy), or the like is used as a group V raw material gas.

Furthermore, in a case where an aluminum gallium nitride (AlGaN) film is formed, it is possible to use the above-mentioned raw material gases that are used for forming GaN and AlN films, as group III raw material gases.

Furthermore, in a case where an electron supply layer in an HEMT described below is formed of InGaN, InAlN, InAlGaN, or the like, an In raw material gas is simultaneously supplied in addition to the above-mentioned raw material gasses that are used for forming GaN and AlN films. Trimethylindium (TMI), triethylindium (TEI), or the like is used as an In raw material gas.

In general, film formation in a normal film formation device is conducted based on a predetermined device parameter. However, an analysis device capable of deriving rates of vacancy for a Ga vacancy and an N vacancy and degrees of a disturbance of an atomic position of Ga and a disturbance of an atomic position of N is installed in a film formation device in the present embodiment. Hence, it is possible to apply feedback to a film formation condition for a film formation device based on rates of vacancy for a Ga vacancy and an N vacancy and degrees of a disturbance of an atomic position of Ga and a disturbance of an atomic position of N that are obtained by an analysis device installed therein. Thus, for a film formation condition to be subjected to feedback, it is possible to provide a pressure in the film formation chamber 200, a temperature of a heater part of the electrically conductive sample stage 72, an amount of supply of a raw material gas supplied into the film formation chamber 200, or the like.

Furthermore, a film formation control part 220 is provided in a film formation device in the present embodiment. In the film formation control part 220, a control of a film formation condition such as amounts of supply of a group III raw material gas and a group V raw material gas to be supplied from the gas introduction port 201a and the gas introduction port 201b is conducted based on derived information of rates of vacancy for an N vacancy and a Ga vacancy and degrees of an N disturbance and a Ga disturbance. Thereby, it is possible to obtain a crystal film with even higher quality, so that it is possible to improve a characteristic of an HEMT by using such a high quality film for an electron transit layer in the HEMT and further it is possible to improve a yield thereof.

Figure 16:
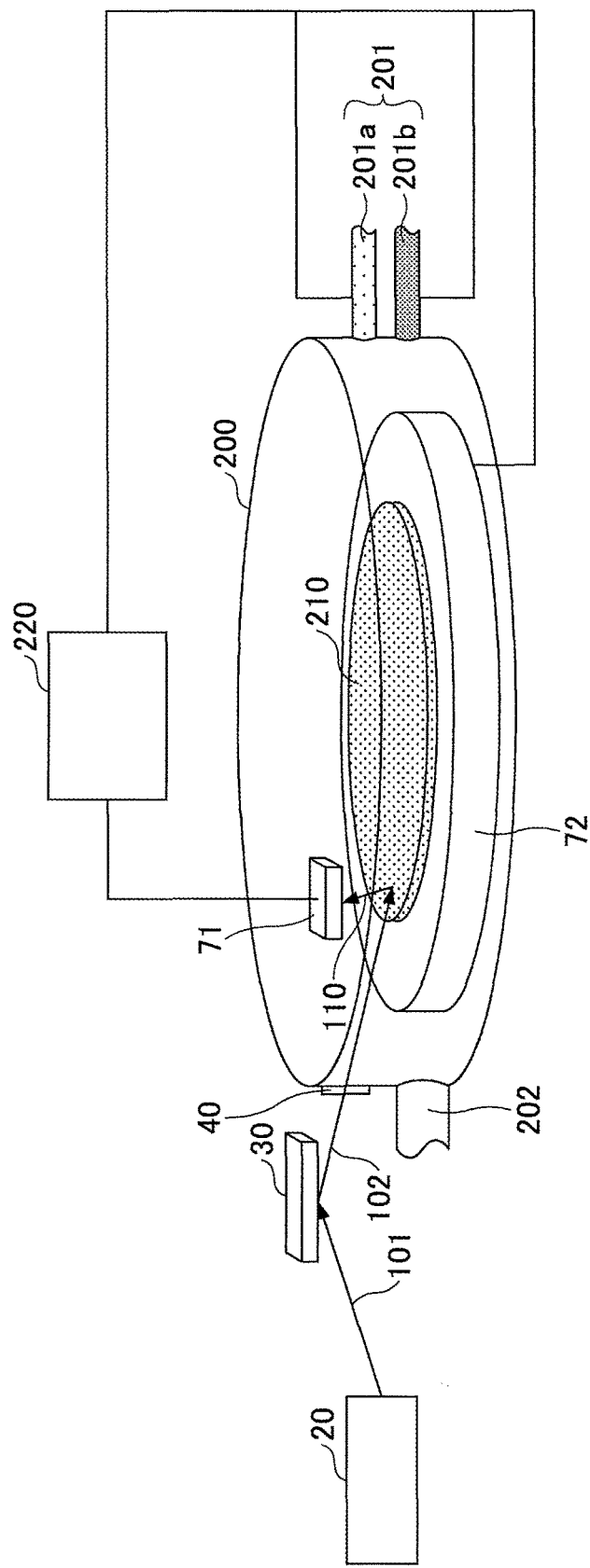
FIG. 16 is a structural diagram of another film formation device in the second embodiment.

Here, although a so-called "vertical-type" MOCVD film formation device has been described with FIG. 15, a film formation device in the present embodiment may be a so-called "horizontal-type" MOCVD film formation device as illustrated in FIG. 16.

(A Method for Fabricating a Semiconductor Device)

Figure 17:
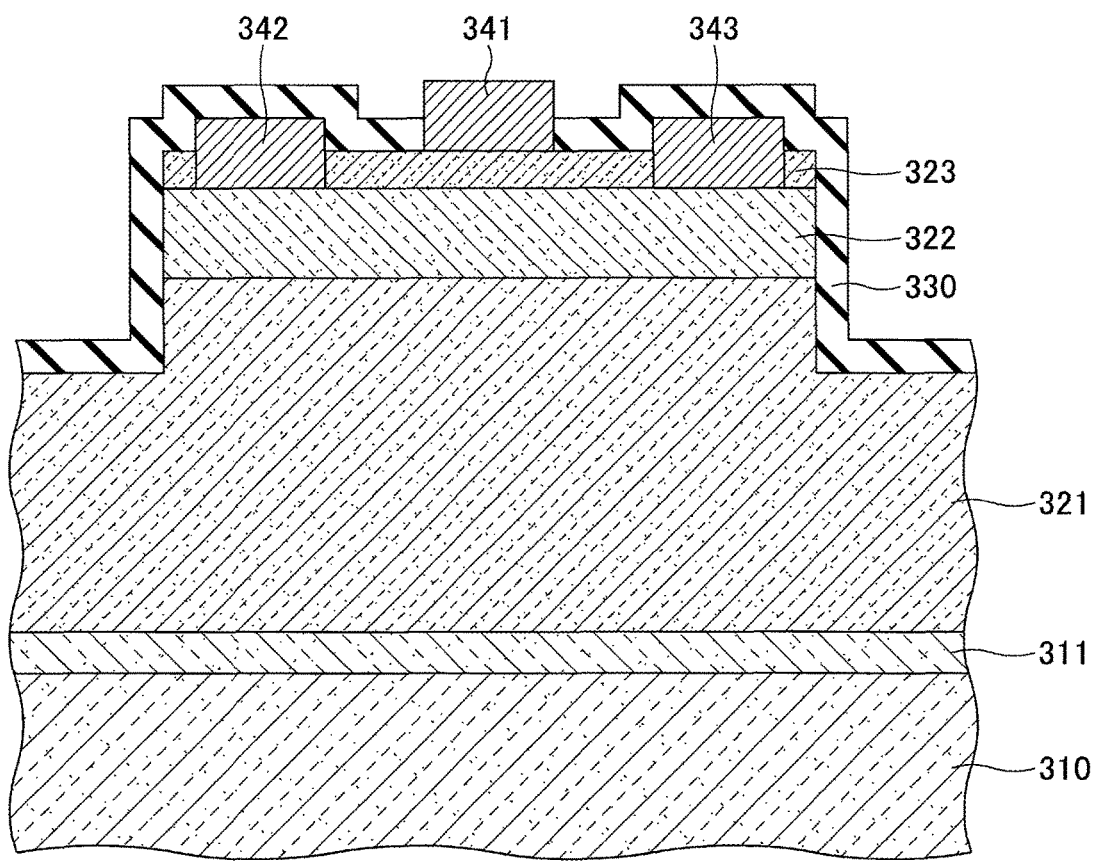
FIG. 17 is a structural diagram of a semiconductor device fabricated in the second embodiment.

Next, a semiconductor device to be fabricated by using a film formation device and a film formation method in the present embodiment will be described based on FIG. 17. A semiconductor device illustrated in FIG. 17 is such that a buffer layer 311, an electron transit layer 321, an electron supply layer 322, and a cap layer 323 are formed of nitride semiconductors on a substrate 310. A gate electrode 341 is formed on the cap layer 323 and a source electrode 342 and a drain electrode 343 are formed on the electron supply layer 322, wherein a passivation film 330 is formed on an area that otherwise exposes a surface of a nitride semiconductor.

Next, a method for fabricating a semiconductor device with a structure illustrated in FIG. 17 will be described.

First, the substrate 310 formed of silicon carbide (SiC) is conveyed by a non-illustrated transfer robot and placed on the electrically conductive sample stage 72 that is provided in the film formation chamber 200 of a film formation device in the present embodiment and doubles as an electrode.

After the substrate 310 is placed on the electrically conductive sample stage 72, $H_2$ gas is supplied into the film formation chamber 200 and a pressure in the film formation chamber 200 is controlled to be 100 Torr by a non-illustrated pressure control valve. After that, a substrate temperature is elevated to 1150° C. and heat-washing of an inside of the film formation chamber 200 is conducted under an $H_2$ atmosphere at 100 Torr for 5 minutes.

After that, tirmethylaluminum (TMA) and ammonia ($NH_3$) are supplied into the film formation chamber 200 and an AlN film with a thickness of about 30 nm is formed on the substrate 310 on film formation conditions that are at a pressure of 100 Torr and a substrate temperature of 1150° C., so that the buffer layer 311 is formed. For forming the buffer layer 311, it is preferable to supply a group III raw material gas and a group V raw material gas separately into the film formation chamber 200 and reduce a pressure in the film formation chamber 200 so that the probability of collision between the group III raw material gas and the group V raw material gas and thereby a gas phase reaction is suppressed.

Furthermore, a molar ratio of N in group V to Al in group III, namely, a V/III ratio was controlled to be 6000. A film formation rate for forming the buffer layer 311 was about 6 nm/minute and a time period of 5 minutes was needed for forming the buffer layer 311 with a thickness of 30 nm. Because the buffer layer 311 composed of AlN has a thickness of 30 nm and is thin, a change in a film formation rate hardly affects a total film formation time period. For this reason, it is preferable to form a film at a low film formation rate so that the buffer layer 311 has little vacancy and little disturbance.

Then, trimethylgallium (TMG) and ammonia ($NH_3$) are supplied into the film formation chamber 200 and a GaN film with a thickness of 3 μm is formed on the buffer layer 311 on a film formation condition that is a substrate temperature of 1050° C., so that the electron transit layer 321 is formed. Because the electron transit layer 321 formed of GaN is a layer that corresponds to a channel layer and an electron transfers therein, it is preferable to be a high quality film. In general, when a film formation rate is reduced by, for example, increasing a V/III ratio, a film with little vacancy and little disturbance is readily obtained. However, a longer time period is needed for forming the electron transit layer 321, because a film thickness thereof is 100 times to 1000 times greater than that of another nitride semiconductor layer such as the buffer layer 311. For this reason, it is not preferable to reduce a film formation rate for forming the electron transit layer 321 more than necessary, because a fabrication time period is longer and a fabrication cost is also higher. Hence, when the electron transit layer 321 is formed, it is desired that both a film formation rate and a film quality are taken into consideration.

Because a film formation rate for forming the electron transit layer 321 is generally about 50 nm/minute, a film formation time period of about 1 hour is needed in order to form the electron transit layer 321. In the present embodiment, a film formation is conducted while a rate of vacancy in the electron transit layer 321 is measured, and a V/III ratio is changed depending on a measured rate of vacancy. Thereby, it is possible to increase a film formation rate in a possible range while a film quality of the electron transit layer 321 to be formed is kept at a constant or higher. Thus, it is possible for the present embodiment to attain a balance between a film formation rate and a film quality when the electron transit layer 321 is formed.

In the present embodiment, confirmation of a rate of vacancy at a time when the electron transit later 321 was formed is conducted for a Ga vacancy and a control was made in such a manner that a density of the Ga vacancy was not greater than $1 \times 10^{17}$ $cm^{-3}$. A film formation rate started at 10 nm/minute at first, was increased gradually, and could be increased to be 200 nm/minute finally. Thereby, it was possible to reduce a film formation time period of the electron transit layer 321 to be about 20 minutes, although about 1 hour was needed usually. Here, if a density of Ga vacancy of $1 \times 10^{18}$ $cm^{-3}$ is not problematic in a fabricated HEMT, it is possible to conduct a film formation of the electron transit layer 321 at a higher speed.

Although a case where a control is conducted with reference to a density of a Ga vacancy as an index has been described in the above description, it is also possible to conduct a control with reference to any of four indices because any of an N vacancy, a Ga disturbance, and an N disturbance is better by increasing a V/III ratio. Furthermore, it is also possible to determine an upper limit value of each of densities of vacancy for and disturbances of atomic positions of Ga and N and conduct a control to satisfy any of them.

Then, a n-AlGaN film with a thickness of about 20 nm is formed on the electron transit layer 321 so that the electron supply layer 322 is formed. When n-AlGaN layer was formed, doping with Si as an impurity element that provided an n-type was conducted in such a manner that an impurity concentration was $1 \times 10^{18}$ $cm^{-3}$. Silane ($SiH_4$) was used as a raw material gas for adding Si thereto.

Then, a n-GaN film with a thickness of about 5 nm is formed on the electron supply layer 322 so that the cap layer 323 is formed. After that, the cap layer 323 in an area where the source electrode 342 and the drain electrode 343 are formed is eliminated by etching in such a manner that a surface of the electron supply layer 322 is exposed. After that, the source electrode 342 and the drain electrode 343 are formed in an area where the electron supply layer 322 is exposed. The source electrode 342 and the drain electrode 343 are formed by metal lamination films of Ti/Al, wherein a film thickness of a formed Ti film is about 15 nm and a film thickness of an Al film is about 150 nm. After that, heat treatment was conducted to provide a ohmic contact.

Then, an SiN film with a thickness of 20 nm is formed on the cap layer 323 or the like so that the passivation film 330 is formed. After that, the passivation film 330 in an area where the gate electrode 341 is formed is eliminated by etching in such a manner that a surface of the cap layer 323 is exposed, and the gate electrode 341 is formed on an exposed cap layer 323. The gate electrode 341 is formed of a metal lamination film of Ni/Au, wherein a film thickness of a formed Ni film is about 15 nm and a film thickness of an Au film is about 200 nm. Moreover, an element separation area, a wiring, a protective film, and the like were formed to fabricate an HEMI that was a semiconductor device.

When a semiconductor device with a structure illustrated in FIG. 17 was fabricated by a film formation device in the present embodiment, a film formation rate was controlled by conducting a measurement of a Ga vacancy. Furthermore, a film formation parameter to be controlled may be a substrate temperature. In a case where a substrate temperature is controlled, when the substrate temperature is increased, a density of an N vacancy is increased whereas a density of a Ga vacancy is reduced. For this reason, it is possible to form the electron transit layer 321 composed of a high quality GaN by measuring both a rate of vacancy for a Ga vacancy and a rate of vacancy for an N vacancy and conduct a control to provide a balanced film with a Ga vacancy and an N vacancy that are little.

Furthermore, the electron transit layer 321 composed of GaN may be formed on a condition that an inside of the film formation chamber 200 is under a reduced pressure in order to suppress a gas phase reaction. However, it is preferable to conduct growth on a condition that a pressure in the film formation chamber 200 is a high pressure in order to suppress an N vacancy, because a vapor pressure of N that is a structural element of GaN forming the electron transit layer 321 is very high. In this case, for example, if it is possible to measure a rate of vacancy for an N vacancy, it is also possible to set an upper limit value of the rate of vacancy for the N vacancy and control a pressure in the film formation chamber 200 based on this upper limit value.

Moreover, although a case where film formation of the electron supply layer 322 composed of n-AlGaN is conducted immediately after the electron transit layer 321 composed of GaN is formed has been described in the above description, a vacancy may frequently increase in a temperature lowering process in a case of lowering a temperature or the like. However, because it is possible to lower a temperature in a case of a film formation device in the present embodiment while a rate of vacancy for a vacancy is confirmed, it is possible to provide a measure, for example, increase a pressure in the film formation chamber 200 at a time of temperature lowering or the like.

According to a disclosed analysis method and analysis device, it is possible to measure a rate of vacancy and a disturbance of an atomic position for each element in a III-V compound semiconductor such as GaN.

All examples and conditional language provided herein are intended for the pedagogical purposes of aiding the reader in understanding the invention and the concepts contributed by the inventor to further the art, and are not to be construed as limitations to such specially recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An analysis device comprising:
   an X-ray generation part configured to generate four monochromatic X-rays with different energies to irradiate a sample;
   an electrically conductive sample stage configured to place the sample thereon and formed of an electrically conductive material;
   an electrode configured to detect an electric current carried by irradiating the sample with the four monochromatic X-rays with different energies; and
   an electric power source configured to apply a voltage between the electrically conductive sample stage and the electrode,
   wherein the four monochromatic X-rays with different energies are X-rays included within a range from an absorption edge of a compound semiconductor included in the sample to a higher energy side of 300 eV.

2. The analysis device as claimed in claim 1, comprising a control part configured to calculate a rate of vacancy and a degree of disturbance of an atomic position for an element composing the compound semiconductor based on an electric current carried through the electrode.

3. The analysis device as claimed in claim 1, wherein three of the four monochromatic X-rays with different energies are a monochromatic X-ray with an energy value of 10392 eV or greater and 10402 eV or less, a monochromatic X-ray with an energy value of 10540 eV or greater and 10550 eV or less, and a monochromatic X-ray with an energy value of 10427 eV or greater and 10437 eV or less, and the remaining one is a monochromatic X-ray with an energy value of 10469 eV or greater and 10479 eV or less or a monochromatic X-ray with an energy value of 10399 eV or greater and 10409 eV or less.

4. The analysis device as claimed in claim 1, wherein the X-ray generation part includes an X-ray source configured to emit an X-ray and a monochromator configured to provide the four monochromatic X-rays with different energies from the X-ray emitted from the X-ray source.

5. The analysis device as claimed in claim 4, wherein the monochromator is provided with four monochromatic function parts configured to provide the four monochromatic X-rays with different energies and each of the four monochromatic X-rays with different energies is obtained by each of the monochromatic function parts.

6. The analysis device as claimed in claim 1, wherein the compound semiconductor is a nitride semiconductor.

7. The analysis device as claimed in claim 1, wherein the compound semiconductor includes GaN.

8. A film formation device comprising:
   the analysis device as claimed in claim 1;
   a gas supply port configured to supply a raw material gas configured to form a film of a compound semiconductor; and
   a film formation control part configured to control an amount of supply of the raw material gas supplied from the gas supply port,
   wherein the film formation control part is configured to control the amount of supply of the raw material gas based on a rate of vacancy and a degree of disturbance of an atomic position for an element composing the compound semiconductor calculated in the control part.

* * * * *